United States Patent
Spagnoli et al.

(10) Patent No.: US 10,526,577 B2
(45) Date of Patent: Jan. 7, 2020

(54) TGIF2-INDUCED REPROGRAMMING OF HEPATIC CELLS TO PANCREATIC PROGENITOR CELLS AND MEDICAL USES THEREOF

(71) Applicant: MAX-DELBRUECK-CENTRUM FUER MOLEKULARE MEDIZIN, Berlin (DE)

(72) Inventors: Francesca Spagnoli, Berlin (DE); Nuria Cerda-Esteban, Berlin (DE)

(73) Assignee: MAX-DELBRUECK-CENTRUM FUER MOLEKULARE MEDIZIN, Berlin (DE)

( * ) Notice: Subject to any disclaimer, the term of this patent is extended or adjusted under 35 U.S.C. 154(b) by 0 days.

(21) Appl. No.: 14/800,880

(22) Filed: Jul. 16, 2015

(65) Prior Publication Data
US 2016/0017289 A1    Jan. 21, 2016

(30) Foreign Application Priority Data

Jul. 16, 2014   (EP) .................................... 14177287

(51) Int. Cl.
| | |
|---|---|
| A61K 48/00 | (2006.01) |
| C12N 5/02 | (2006.01) |
| C12N 5/071 | (2010.01) |
| A61K 35/39 | (2015.01) |
| A01K 67/027 | (2006.01) |
| A01K 67/00 | (2006.01) |

(52) U.S. Cl.
CPC ........ *C12N 5/0678* (2013.01); *A01K 67/0276* (2013.01); *A61K 35/39* (2013.01); *A01K 2217/075* (2013.01); *A01K 2217/15* (2013.01); *A01K 2217/206* (2013.01); *A01K 2267/0362* (2013.01); *C12N 2501/60* (2013.01); *C12N 2501/70* (2013.01); *C12N 2506/14* (2013.01); *C12N 2510/00* (2013.01); *C12N 2740/16043* (2013.01); *C12N 2750/14143* (2013.01); *C12N 2750/14171* (2013.01); *C12N 2830/008* (2013.01)

(58) Field of Classification Search
CPC .............. C12N 5/0678; C12N 2510/00; C12N 2750/14143; A61K 35/39
See application file for complete search history.

(56) References Cited

U.S. PATENT DOCUMENTS

| | | | | |
|---|---|---|---|---|
| 7,282,199 B2 * | 10/2007 | Gao | ..................... | C07K 14/755 424/93.1 |
| 2008/0267928 A1 * | 10/2008 | Yang | ..................... | C12N 5/0676 424/93.21 |
| 2010/0137202 A1 * | 6/2010 | Yang | ..................... | A61K 48/005 514/21.5 |
| 2014/0045923 A1 * | 2/2014 | Anguela Martinez | ..................... | A61K 48/005 514/44 R |

FOREIGN PATENT DOCUMENTS

| | | |
|---|---|---|
| WO | 2009/126927 A2 | 10/2009 |
| WO | 2013/013105 A2 | 1/2013 |

OTHER PUBLICATIONS

Spagnoli F M & Brivanlou A: "The Gata5 target, TGIF2, defines the pancreatic region by modulating BNP signals within the endoderm", in: Development, vol. 135, No. 3, Feb. 2008, pp. 451-461.

Cerdá-Esteban N & Spagnoli F M: "Glimpse into Hox and late regulation of cell differentiation and reprogramming", Developmental Dynamics, vol. 243, No. 1, Jan. 2014, pp. 76-87.

* cited by examiner

*Primary Examiner* — Quang Nguyen
(74) *Attorney, Agent, or Firm* — Agris & Von Natzmer, LLP; Joyce Von Natzmer

(57) ABSTRACT

Disclosed are genetically modified human pancreatic progenitor cells having an exogenous nucleic acid molecule encoding TGIF2, for use as a medicament in the treatment of a subject with diabetes. In addition methods for the production of such cells are described. Also disclosed is an expression vector encoding TGIF2 for use as a medicament in the treatment of a subject with diabetes.

11 Claims, 12 Drawing Sheets
Specification includes a Sequence Listing.

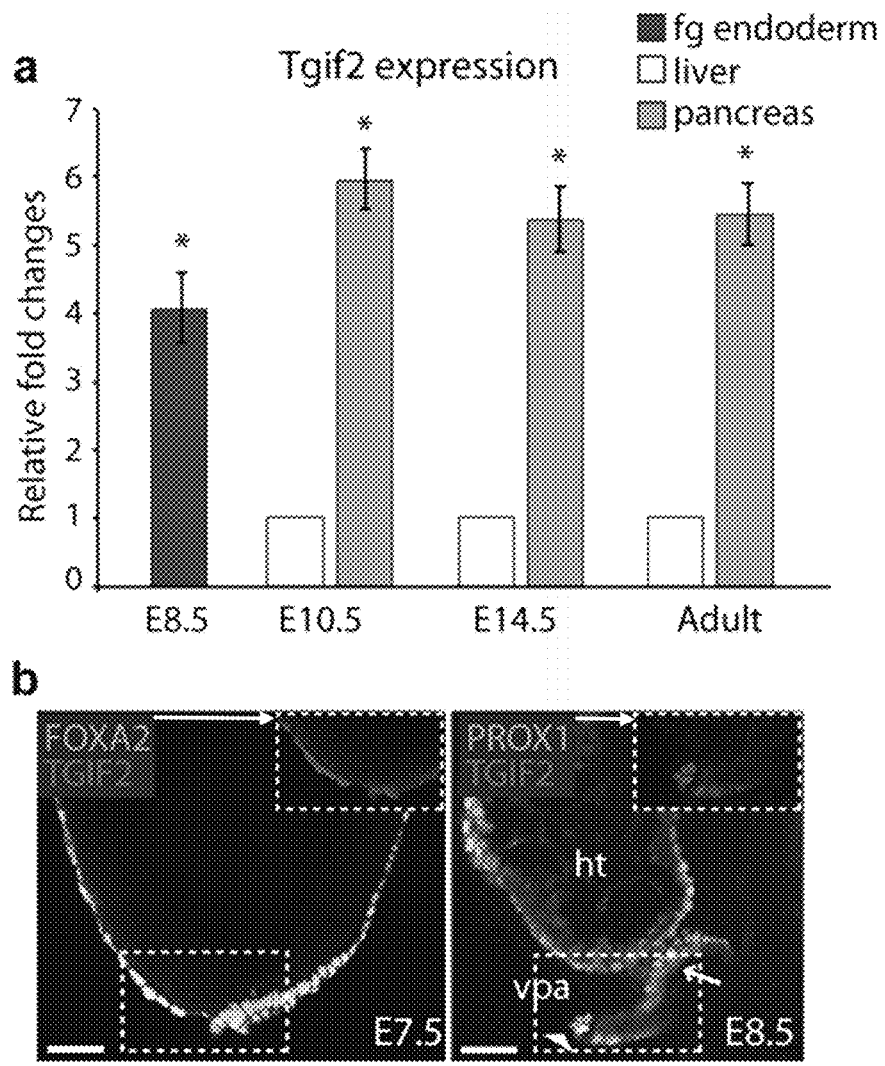

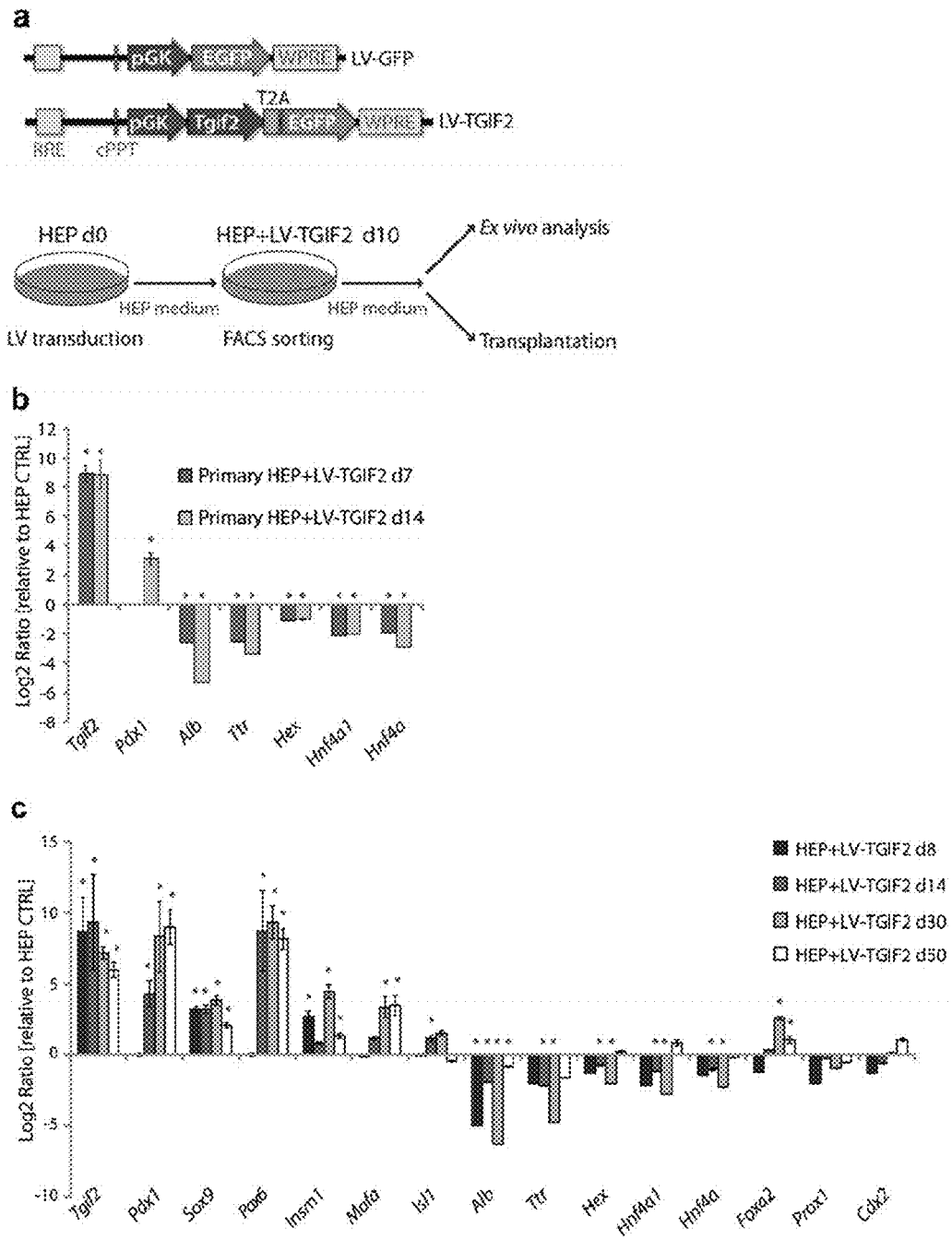

TGIF2-INDUCED REPROGRAMMING OF HEPATIC CELLS TO PANCREATIC PROGENITOR CELLS AND MEDICAL USES THEREOF

CROSS REFERENCE TO RELATED APPLICATIONS

This is a non-provisional application which claims priority from European Patent application EP 14177287.1, filed Jul. 16, 2014 and which is incorporated herein by reference in its entirety.

FIELD OF THE INVENTION

The invention relates to genetically modified human pancreatic progenitor cells, comprising an exogenous nucleic acid molecule encoding TGIF2 (TGFB-induced factor homeobox 2), e.g., for use as a medicament in the treatment of/for administration to a subject with, in particular, diabetes, in addition to methods for the production of said cells. The invention is also directed at viral expression vectors encoding TGIF2 for use as a medicament in the treatment of/for administration to a subject with, in particular, diabetes.

BACKGROUND AND INTRODUCTION TO THE INVENTION

Diabetes mellitus (DM), also known as simply diabetes, is a group of metabolic diseases in which there are high blood sugar levels over a prolonged period. Globally, as of 2013, an estimated 382 million people have diabetes worldwide. In 2012 and 2013 diabetes resulted in 1.5 to 5.1 million deaths per year worldwide, making it the 8th leading cause of death. Novel approaches are required for effective treatment.

Islet transplantation has emerged as a potential therapeutic approach for diabetes and involves the transplantation of isolated islets from a donor pancreas to another person. Once transplanted, the islets begin to produce insulin, actively regulating the level of glucose in the blood. If transplanted cells are not from a genetically identical donor transplant rejection may occur. To prevent this, immunosuppressant drugs are administered, causing a number of unwanted and detrimental side effects. Two critical limitations to islet transplantation are the currently inadequate means for preventing islet rejection, and the limited supply of islets for transplantation. Novel sources of therapeutic cells, in particular autologous cells, are required in order to reduce unwanted side effects and increase efficacy of treatment. One option for the provision of such material is lineage re-programming of non-pancreas cells into pancreas cells.

During embryonic development, cells become gradually restricted in their developmental potential to ultimately acquire a mature differentiated state (reference 1). Seminal work has demonstrated that stable differentiated states can be unlocked and cells can be forced to change their identity either to revert to a pluripotent state or to acquire another differentiated state, a process called lineage reprogramming (references 1, 2, 3). Successful lineage reprogramming relies on the identification of defined factor(s) able to establish the new cell fate transcriptional program and, concomitantly, silence the original gene expression program (references 2, 4, 5, 6).

The references indicated by numerals, for which full citations are provided below under the heading "References" are incorporated herein by reference in their entirety.

Lineage re-programming represents a promising approach for the production of cells for administration in cellular therapy and for the manipulation of cell fate in vivo. Due to the difficulties inherent in obtaining sufficient cell numbers and types for implantation, or in replenishing vital cell types in vivo that may be malfunctioning, re-programming approaches provide advantageous therapeutic means based on novel sources of therapeutic cellular material. The present invention provides tools for manipulating cellular plasticity between liver and pancreas cells, in addition to methods, cells and therapeutic approaches based on the products of fate interconversion between these two cell types.

Evidence of significant plasticity in the adult pancreas has been reported (references 7, 8). In particular, fate interconversion between different pancreatic cell types can occur under extreme beta-cell damage (references 7, 9, 10) or be forced by the expression of pancreatic and/or beta-cell transcription factors (references 8, 11, 12, 13, 14, 15). From a clinical perspective, adult liver cells have some advantages over pancreatic cells, representing a more easily accessible and abundant starting cell population for fate conversion approaches to generate pancreatic cells with therapeutic potentials (references 2, 16). Nevertheless, ectopic expression of pancreatic transcription factors (e.g. Pdx1) in liver appears inadequate, resulting in incomplete phenotypic conversion and hybrid phenotypes (references 16, 17, 18, 19, 20, 21). These observations are consistent with the fact that the two lineages are closely related but yet at a greater distance than cells of the same lineage, e.g. exocrine and endocrine pancreas cells (references 22, 23). Additional limitations might be the lack of appropriate interaction partners or the presence of antagonistic factors in liver cells that lock cell identity, hampering cell plasticity and conversion.

To overcome these lineage restrictions, the present invention is based on the use of regulator(s) of the pancreas versus liver fate decision that act upstream of Pdx1 in the specification cascade, thereby providing effective reprogramming determinants for achieving full conversion of liver cells into pancreas cells of therapeutic relevance.

SUMMARY OF THE INVENTION

There is a need in the art to provide improved or alternative approaches for treating diabetes. There is among others a need to provide regulators of the pancreas versus liver fate decision that enable the production of pancreas cells of therapeutic relevance from non-pancreatic cells. The present invention addresses these and other needs in the art.

The invention relates, in one embodiment, to genetically modified pancreatic progenitor cells, comprising an exogenous nucleic acid molecule encoding TGIF2, for use as a medicament in the treatment of a subject with diabetes or a pre-diabetic subject, wherein said cells are capable of in vivo differentiation into the endocrine Beta-cell lineage. In one embodiment, the cells do differentiate in vivo into the Beta-cell lineage post-administration.

The genetically modified pancreatic progenitor cells are preferably human cells. The exogenous nucleic acid molecule of the genetically modified pancreatic progenitor cells may consist of or consist essentially of exogenous nucleic acid molecule encoding TGIF2.

The invention also relates to a method for the treatment of a subject with diabetes or a pre-diabetic subject, comprising the administration of genetically modified human pancreatic progenitor cells, said cells comprising an exogenous nucleic acid molecule encoding TGIF2, wherein said cells are capable of in vivo differentiation into the endocrine Beta-cell lineage. In one embodiment, the cells do differentiate in vivo into the Beta-cell lineage. References throughout the specification to genetically modified pancreatic progenitor cells for use as a medicament in the treatment of a subject also relate to a method of treatment comprising administration of said cells to said subjects, preferably in a diabetes or a pre-diabetes treating effective amount.

According to the present invention the use of TGIF2 expression for hepatic to pancreatic re-programming may be referred to as TGIF2-induced reprogramming. The pancreatic progenitor cells of the invention may be referred to as TGIF2-induced pancreatic progenitor cells, or abbreviated as "TiPP". TGIF2-induced pancreatic progenitor cells may be produced in vitro, preferably via the methods disclosed herein encompassing the transformation of isolated hepatic cells with an exogenous nucleic acid encoding TGIF2, or in vivo, preferably by administration of a nucleic acid vector encoding TGIF2 to a subject. The nucleic acid/vector is preferably administered in an amount that is effective to cause in-vivo reprogramming of human adult hepatic cells to pancreatic progenitor cells and differentiation of said cells into the endocrine Beta-cell lineage.

A progenitor cell as used herein refers to a biological cell that has not fully differentiated into a specific lineage end-point. The progenitor cells described herein may be considered to be at an intermediate state of differentiation between stem cells and fully differentiated cells. Typically, the potency of a progenitor cell depends on the type of cell and their niche in vivo. In a preferred embodiment, the pancreatic progenitor cells described herein show self-renewal in vitro. In a preferred embodiment the pancreatic progenitor cells described herein show unipotency towards the endocrine Beta-cell lineage. The pancreatic progenitor cell may, e.g., be produced from hepatic cells, in particular, human hepatic cells according to the methods described herein in which, e.g., certain liver-specific gene are repressed and/or certain pancreas-specific genes are activated.

TGIF2 relates to the Three-amino-acid-loop-extension (TALE) homeobox transcription regulator TG-interacting factor 2. In general, TGIF2 exhibits a distinct expression signature at the cell-fate branchpoint, being expressed in the common endoderm progenitor pool, and whose expression changes in opposite directions as cells commit to pancreatic or hepatic lineages (references 24, 26).

In one embodiment of the invention TGIF2 relates to human TGIF2 protein, as described by the National Center for Biotechnology Information, U.S. National Library of Medicine (NCBI), such as according to NCBI Reference Sequence: NP_001186443 (SEQ ID No. 1).

In one embodiment of the invention TGIF2 relates to a human TGIF2 encoding nucleic acid, such as described by the NCBI according to NCBI Reference Sequence: NM_001199514 (SEQ ID No. 2).

In one embodiment of the invention TGIF2 relates to mouse TGIF2 protein, such as described by the NCBI according to NCBI Reference Sequence: NP_775572 (SEQ ID No. 3).

In one embodiment of the invention TGIF2 relates to mouse TGIF2 encoding nucleic acid, such as described by the NCBI according to NCBI Reference Sequence: NM_173396 (SEQ ID No. 4).

The invention described herein, encompassing both in vitro and in vivo TGIF2-induced re-programming of hepatic cells to pancreatic progenitor cells and their medical use, is generally characterized by the unexpected and advantageous finding that TGIF2-induced pancreatic progenitor cells are capable of differentiation/do differentiate into the endocrine Beta-cell lineage. The present invention is based on the finding that TGIF2 expression (in one embodiment as the only medically relevant functional exogenous nucleic acid element) in hepatic cells is sufficient to produce cells that show sufficient pancreatic precursor identity to ultimately differentiate into functional pancreatic cells capable of/inducing the desired in vivo effect of insulin production and blood sugar regulation. The observation of in vivo differentiation of the pancreatic progenitor cells as described herein into the endocrine Beta-cell lineage represents an unexpected finding.

According to the present invention, the cells and therapeutic approaches as described herein are preferably defined by differentiation of the pancreatic progenitor cells into the endocrine Beta-cell lineage. Differentiation into the endocrine Beta-cell lineage may be assayed by assessment of functional cells when implanted in vivo (references 38, 39). To assess the in vivo differentiation potential of the reprogrammed-derived pancreatic progenitor cells can be implanted under the kidney capsule of hyperglycemic Akita mice (as described in more detail below). Islets from Akita heterozygous mice are depleted of beta-cells, and the remaining beta-cells release very little mature insulin, representing an excellent mouse model of diabetes[43]. Differentiation into the endocrine Beta-cell lineage may be observed when cells implanted under the kidney capsule organize into epithelial structures. Such structures preferably express Sox9, E-cadherin and/or insulin. Insulin production alone may be used as a read-out for endocrine Beta-cell lineage differentiation. A further indication of pancreatic progenitor cells, that are capable of differentiation into the endocrine Beta-cell lineage, is the presence of cytoplasmic endocrine granules in cells in vitro, as shown herein. In a preferred embodiment the method to determine differentiation to the "endocrine Beta-cell lineage", or the capability of cells to show such differentiation, is by correction or amelioration of the blood glucose levels of the diabetic mice after administration of suitable cells. An example of this test is provided in the examples below, in particular with reference to FIG. 4a.

In a preferred embodiment the genetically modified pancreatic progenitor cells of the present invention are characterized in that said cells are autologous with respect to the subject of medical treatment. As used herein, a cell is "autologous" with respect to a subject if it or its precursor cells are obtained from the same subject. Allogenic cells may be used in the present invention, for example when an appropriate matching strategy for allogenic patient compatibility and/or suitable means for reducing risk of transplantation rejection are employed. As used herein, a cell is "allogenic" with respect to a subject if it or any of its precursor cells are from another subject of the same species.

The exogenous nucleic acid encoding TGIF2 is, in a preferred embodiment, defined by the capability of expressing TGIF2, preferably by combining a suitable promoter with the TGIF2-encoding sequence, so that the promoter and TGIF2-encoding sequence are operably linked. The term "operably linked" refers to a functional combination between promoter and coding sequence enabling transcription of the coding nucleic acid.

In a preferred embodiment the genetically modified pancreatic progenitor cells of the present invention are characterized in that the exogenous nucleic acid comprises a stably integrated lentiviral vector encoding TGIF2. According to the present invention, stable integration of an exogenous relates to a genetic modification of a chromosome of a cell, wherein said modification is maintained during cell division via chromosomal replication. In a non-limiting and preferred embodiment the vector used in the present examples relates to the pRRL.SIN.cPPT.PGK-GFP.WPRE lentiviral plasmid vector (obtained from ADDGENE; plasmid 12252). This vector is suitable for use in humans.

In one embodiment the genetically modified pancreatic progenitor cells of the present invention are characterized in that the exogenous nucleic acid comprises the phosphoglycerate kinase-1 (PGK) promoter operably linked to the TGIF2-coding nucleic acid sequence. The PGK promoter is a constitutive promoter that is not intended as a limiting embodiment of the invention. Alternative constitutive promoters are known in the art that may be used in the present invention.

In one embodiment the genetically modified pancreatic progenitor cells of the present invention are characterized in that the exogenous nucleic acid comprises the Human thyroxine binding globulin promoter (TBG) promoter operably linked to the TGIF2-coding nucleic acid sequence. The TBG promoter is liver-specific and is preferred for in vivo applications.

Genetically modified pancreatic progenitor cell (TGIF2-induced; TiPP) for use as a medicament according to any one of the preceding claims, wherein said treatment comprises cellular therapy, comprising preferably intravenous administration of said cells. Any given form of cellular therapy is encompassed by the present invention. Intravenous is one possible and preferred method of administration that shows beneficial properties.

In one embodiment the genetically modified pancreatic progenitor cells of the present invention are characterized in that said cells are obtained from (or obtainable from) human adult hepatic cells, preferably via TGIF2-induced re-programming. TGIF2-induced reprogramming relates to the expression of TGIF2 from an exogenous nucleic acid as described herein.

The progenitor cells of the present invention display a remarkable and unexpected re-programming towards pancreatic progenitor cells. The source of said cells is preferably adult human hepatic cells, for example those obtained from a liver biopsy. Although the re-programming to a pancreatic progenitor appears to be effectively (largely) complete, there may in some embodiments be an indication of the original source of the cell. It is conceivable that the pancreatic progenitor cell may be characterised by one or more molecular and/or structural features of the original hepatic cell, for example by lingering hepatic markers, expressed at a (severely) reduced extent in comparison to the original isolated hepatic cells, but still detectable in comparison to either terminally differentiated pancreatic cells or fetal pancreatic precursor cells.

In one embodiment the cells as such may be defined by their origin (human adult hepatic cells), without limitation to the method of their production or particular source. The molecular details of re-programming from hepatic to pancreatic cell fates represents a potentially complex cellular event or process, leading to a unique set of structural and/or molecular features, by which the cells themselves may be characterized.

The invention therefore also relates to human adult hepatic cells that comprise an exogenous nucleic acid molecule encoding TGIF2, before said re-programming as described herein has taken place.

In a preferred embodiment the genetically modified pancreatic progenitor cells of the present invention are characterized by repression of liver-specific gene expression and activation of pancreas-specific gene expression. The individual markers and combinations of markers provided herein enable determination of the cells of the present invention.

In a preferred embodiment, said repression of liver-specific gene expression comprises repression of Albumin, Transthyretin (Ttr) and/or Serpina 1. In a preferred embodiment, said repression of liver-specific gene expression comprises repression of one or more of Albumin, Transthyretin (Ttr), Serpina 1, Hex, Hnf4-alpha and/or Hnf4-alpha1 liver-specific isoform. These markers are conserved in both human subjects and mouse models. In a preferred embodiment at least 1, preferably at least 2, 3, 4, or more preferably at least 5, or all, of said liver-specific markers are repressed in said cells.

In a preferred embodiment, said activation of pancreas-specific gene expression comprises activation of Pdx1, Sox9, Pax6 and/or Ptf1a. In a preferred embodiment, said activation of pancreas-specific gene expression comprises activation of one or more of Pdx1, Sox9, Insm1, Pax6, Ptf1a, Onecut1, Nr5a2, RbpJ, Tle2, Tle3 and/or MafA. These markers are conserved in both human subjects and mouse models. In a preferred embodiment at least 1, preferably at least 2, 3, 4, 5, 6, 7, 8, 9 or preferably at least 10, or all, of said liver-specific markers are expressed in said cells.

In a further aspect, the invention relates to an in vitro method for the production of genetically modified human pancreatic progenitor cells, preferably according to any one of the preceding claims (TGIF2-induced; TiPP), wherein said cells are capable of differentiation into the endocrine Beta-cell lineage, comprising
  a. Providing human adult hepatic cells;
  b. Transformation of said cells with an exogenous nucleic acid encoding TGIF2, preferably comprising stable integration of a lentiviral vector;
  c. Re-programming of said cells to pancreatic progenitor cells (TGIF2-induced; TiPP).

The method of the present invention provides a novel method of manufacture for therapeutic progenitor pancreatic cells. The method as described may also encompass the subsequent preparation of a medicament comprising provision of the cells in a pharmaceutically acceptable composition with one or more pharmaceutically acceptable carrier substances.

In a preferred embodiment the in vitro method as described herein is characterized in that step a) comprises providing cells obtained from a liver biopsy. As mentioned above, from a clinical perspective, adult liver cells have advantages over pancreatic cells, representing a more easily accessible and abundant starting cell population for fate conversion approaches to generate pancreatic cells with therapeutic potentials (references 2, 16). The method may incorporate obtaining the human adult hepatic cells. Suitable methods for liver biopsy are known to one skilled in the art. In some embodiments, non-invasive procedures may be employed without significant risk to the health of the subject. In a preferred embodiment the cells are autologous with respect to the intended patient.

One non-limiting example of the invention relates to carrying out, or using cells already obtained from, a liver biopsy. Percutaneous liver biopsy is one potential embodiment, otherwise known as a transthoracic (transpleural or transparietal) and subcostal liver biopsy, which involves a procedure in which a long needle is introduced through the skin, subcutaneous tissues, intercostal muscles, and peritoneum into the liver to obtain a specimen of liver tissue. Liver biopsy may also be carried out using transvenous or laproscopic approaches.

In a preferred embodiment the in vitro method as described herein is characterized in that re-programming comprises:
 a. repression of liver-specific gene expression, characterised preferably by repression of Albumin, Transthyretin (Ttr), Hex, Hnf4-alpha and/or Hnf4-alpha1 liver-specific isoform; and
 b. activation of pancreas-specific gene expression, characterised preferably by activation of Pdx1, Sox9, Insm1, Pax6, Ptf1a, Onecut1, Nr5a2, RbpJ, Tle2, Tle3 and/or MafA.

The method may also comprise the selection of re-programmed cells according to the absence (of liver-specific) or presence (of pancreas-specific) of any one or more of the markers provided herein. Such cell selection may be carried out according to standard techniques, such as FACS.

The re-programming step d) may also comprise culturing of said cells in vitro. Transformed cells that have been re-programmed to the pancreatic progenitor state do exhibit self-renewal in culture. In one embodiment the culture conditions for re-programmed cells relate to the same conditions used for isolate hepatocytes. Re-programmed or hepatic cells may for example be cultured on Collagen I-coated plates in William's E medium (Sigma) supplemented with 2 mM Glutamax™, 10% FBS (PAN Biotech™), 30 ng/mL IGF II (PeproTech™), 50 ng/mL EGF (PeproTech™), 10 µg/mL Insulin (Roche), 0.1 µm dexamethasone (Sigma) and 10 µm nicotinamide (SIGMA). However, TGIF2-mediated reprogramming is improved in medium depleted of insulin, IGF II and/or dexamethasone (referred to herein as "modified medium").

In a further aspect the invention relates to an expression vector encoding TGIF2 for use as a medicament in the treatment of a subject with diabetes, said treatment comprising in vivo re-programming of human adult hepatic cells to pancreatic progenitor cells and differentiation of said cells into the endocrine Beta-cell lineage.

The invention therefore relates to a method for the treatment of a subject with diabetes comprising administering an expression vector encoding TGIF2, said treatment comprising in vivo re-programming of human adult hepatic cells to pancreatic progenitor cells and differentiation of said cells into the endocrine Beta-cell lineage.

Expression vectors suitable for administration in humans are known to a skilled person. In a preferred but non-limiting embodiment the expression vector is a viral vector. In a further preferred embodiment the viral vector is an adeno-associated viral vector (AAV). As disclosed in the experimental examples herein, a preferred but non-limiting embodiment relates to the use of the AAV serotype 8 (AAV2/8) vector. AAV are derived from human parvovirus. The recombinant AAV serotypes are replication-defective, generally do not insert into the host genome and show a lack of pathogenicity and immune response in human subjects.

In a preferred embodiment the expression vector encoding TGIF2 is characterized in that said vector comprises a hepatocyte-specific promoter operably linked to the TGIF2-coding nucleic acid sequence. In one embodiment the hepatocyte-specific thyroid-binding globulin (TBG) promoter is provided as a suitable but non-limiting embodiment in the examples described herein.

In a preferred embodiment the expression vector encoding TGIF2, in particular the medical administration thereof, is characterized in that said treatment comprises:

a. injection of said expression vector into the liver of the recipient subject; and/or
 b. intravenous injection of said expression vector into the recipient subject.

No mention is found in the prior art that the administration of an expression vector encoding TGIF2 is sufficient to enable in vivo re-programming of human adult hepatic cells to pancreatic progenitor cells. Furthermore, the ability of such in vivo re-programmed cells to differentiate into the endocrine Beta-cell lineage, thereby providing a functional medically relevant effect in the context of diabetes treatment, is to the knowledge of the inventors neither suggested nor disclosed in the relevant art.

BRIEF DESCRIPTION OF THE DRAWINGS

The invention is further described by the figures. The figures represent particular embodiments of the invention and are not intended to limit the scope of the invention.

Short Description of the Figures:

FIG. 2. Tgif2 expression induces adult murine liver cells to acquire molecular features of pancreatic progenitors.

DETAILED DESCRIPTION OF VARIOUS AND PREFERRED EMBODIMENTS OF THE INVENTION

Figure 1:
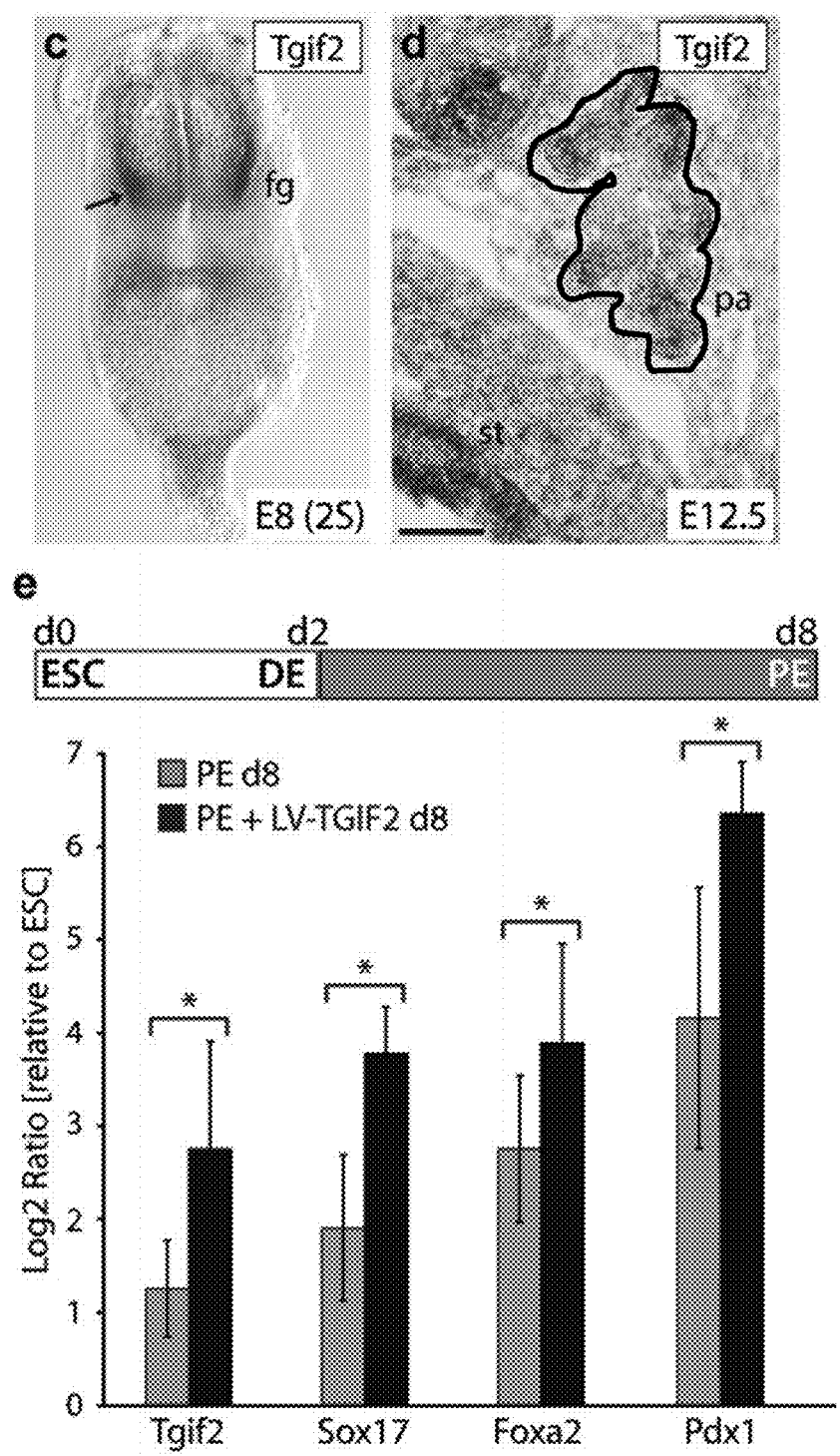
FIG. 1. TGIF2 controls pancreatic and hepatic cell lineage divergence in foregut progenitors.

The liver is an ideal tissue source for generating pancreatic cells, due to its close developmental origin with the pancreas and its regenerative ability. Liver and pancreas arise as mutually exclusive fates from a common endoderm progenitor population in the embryo. Yet, the molecular bases of hepatic and pancreatic cellular plasticity have not been well characterized in the prior art.

The present invention is based on the use of the TALE homeoprotein TGIF2 (TGFB-induced factor homeobox 2; TGFB: transforming growth factor beta) as a developmental regulator of the pancreas versus liver fate decision. TGIF2 is sufficient to elicit liver-to-pancreas fate conversion both ex vivo and in vivo.

Hepatocytes expressing Tgif2 undergo extensive transcriptional remodeling, which erases the original hepatic identity and, over time, induces a pancreatic progenitor phenotype. Consistently, in vivo forced expression of Tgif2 activates pancreatic progenitor genes in adult hepatocytes.

The present invention utilizes the previously unknown and remarkable reprogramming activity of TGIF2 and therefore employs a stepwise lineage reprogramming based on the reversion of lineage decision, thereby enabling a complete or nearly-complete identity switch.

As used herein, "nucleic acid" shall mean any nucleic acid molecule, including, without limitation, DNA, RNA and hybrids or modified variants thereof. An "exogenous nucleic acid" or "exogenous genetic element" relates to any nucleic acid introduced into the cell, which is not a component of the cells "original" genome. Exogenous nucleic acids may be integrated or non-integrated, or relate to stably transfected nucleic acids.

With respect to transformation of cells, either in vitro or in vivo, any given gene delivery method is encompassed by the invention and preferably relates to the use of viral or non-viral vectors, as well as biological or chemical methods of transfection. The methods can yield either stable or transient gene expression in the system used.

Genetically modified viruses have been widely applied for the delivery of genes into cells, both in vitro and in vivo. RNA viruses, such as Lentiviruses, or other retroviruses, may be used in the context of the present invention.

Lentiviruses are members of Retroviridae family of viruses (M. Scherr et al., Gene transfer into hematopoietic stem cells using lentiviral vectors. Curr Gene Ther. 2002 February; 2(1):45-55). Lentivirus vectors are generated by deletion of the entire viral sequence with the exception of the LTRs and cis acting packaging signals. The resultant vectors have a cloning capacity of about 8 kb. One distinguishing feature of these vectors from retroviral vectors is their ability to transduce dividing and non-dividing cells as well as progenitor or terminally differentiated cells.

Non-viral methods may also be employed for genetic transformation, such as alternative strategies that include conventional plasmid transfer and the application of targeted gene integration through the use of integrase or transposase technologies. These represent approaches for vector transformation that have the advantage of being both efficient, and often site-specific in their integration. Physical methods to introduce vectors into cells are known to a skilled person. One example relates to electroporation, which relies on the use of brief, high voltage electric pulses which create transient pores in the membrane by overcoming its capacitance. One advantage of this method is that it can be utilized for both stable and transient gene expression in most cell types. Alternative methods relate to the use of liposomes or protein transduction domains. Appropriate methods are known to a skilled person and are not intended as limiting embodiments of the present invention.

In another aspect, the invention encompasses the use of TGIF2, and in particular nucleic acids encoding TGIF2 selected from the group comprising:
  a) a nucleic acid molecule comprising a nucleotide sequence
  b) which encodes human TGIF2, preferably according to SEQ ID No. 2, or a nucleotide sequence which encodes mouse TGIF2, preferably according to SEQ ID No. 4;
  c) a nucleic acid molecule which is complementary to a nucleotide sequence in accordance with a);
  d) a nucleic acid molecule which undergoes hybridization with a nucleotide sequence according to a) or b) under stringent conditions;
  e) a nucleic acid molecule comprising a nucleotide sequence having sufficient sequence identity to be functionally analogous to a nucleotide sequence according to a), b) or c);
  f) a nucleic acid molecule which, as a consequence of the genetic code, is degenerated in-to nucleotide sequence according to a) through d); and
  g) a nucleic acid molecule according to a nucleotide sequence of a) through e) which is modified by deletions, additions, substitutions, translocations, inversions and/or insertions and functionally analogous to a nucleotide sequence according to a) through e)

Accordingly, the invention encompasses nucleic acid molecules with at least 60%, preferably at least 70%, more preferably at least 80%, especially preferably at least 90%, at least 95% or at least 98% sequence identity to the nucleic acid molecule encoding TGIF2 according to NCBI Reference Sequence: NM_001199514 (SEQ ID No. 2) or NM_173396 (SEQ ID No. 4).

Sequence variants of the claimed nucleic acids and/or proteins, for example defined by the provided % sequence identity, that maintain the said properties of the invention are also included in the scope of the invention. Such variants, which show alternative sequences, but maintain essentially the same properties, such as TGIF2 function, as the specific sequences provided are known as functional analogues, or as functionally analogous. Sequence identity relates to the percentage of identical nucleotides or amino acids when carrying out a sequence alignment, for example using software such as BLAST.

It will be appreciated by those of ordinary skill in the art that, as a result of the degeneracy of the genetic code, there are many nucleotide sequences that encode a polypeptide as described herein. Some of these polynucleotides bear minimal homology or sequence identity to the nucleotide sequence of any native gene. Nonetheless, polynucleotides that vary due to differences in codon usage are specifically contemplated by the present invention. Deletions, substitutions and other changes in sequence that fall under the described sequence identity are also encompassed in the invention.

Protein modifications, which may occur through substitutions, are also included within the scope of the invention. Substitutions as defined herein are modifications made to the amino acid sequence of the protein, whereby one or more amino acids are replaced with the same number of (different) amino acids, producing a protein, which contains a different amino acid sequence than the primary protein, preferably without significantly altering the function of the protein. Like additions, substitutions may be natural or artificial. It is well known in the art that amino acid substitutions may be made without significantly altering the protein's function. This is particularly true when the modification relates to a "conservative" amino acid substitution, which is the substitution of one amino acid for another of similar properties. Such "conserved" amino acids can be natural or synthetic amino acids which because of size, charge, polarity and conformation can be substituted without significantly affecting the structure and function of the protein. Frequently, many amino acids may be substituted by conservative amino acids without deleteriously affecting the protein's function.

In general, the non-polar amino acids Gly, Ala, Val, Ile and Leu; the non-polar aromatic amino acids Phe, Trp and Tyr; the neutral polar amino acids Ser, Thr, Cys, Gln, Asn and Met; the positively charged amino acids Lys, Arg and His; the negatively charged amino acids Asp and Glu, represent groups of conservative amino acids. This list is not exhaustive. For example, it is well known that Ala, Gly, Ser and sometimes Cys can substitute for each other even though they belong to different groups. Variants of TGIF2 are therefore contemplated and encompassed by the invention that show TGIF2 activity even in light of changes in the coding nucleic acid or amino acid sequence of the known and specific TGIF2 described herein.

Preferred Sequences of the Invention:

| SEQ ID No. | Sequence | Description |
|---|---|---|
| 1 | MSDSDLGEDEGLLSLAGKRKRRGNLPKESVKILRDWLYLHRYNAYPSEQ EKLSLSGQTNLSVLQICNWFINARRRLLPDMLRKDGKDPNQFTISRRGGK ASDVALPRGSSPSVLAVSVPAPTNVLSLSVCSMPLHSGQGEKPAAPFPR GELESPKPLVTPGSTLTLLTRAEAGSPTGGLFNTPPPTPPEQDKEDFSSF QLLVEVALQRAAEMELQKQQDPSLPLLHTPIPLVSENPQ | human TGIF2 protein |
| 2 | CCGACGGCCCGCCCCGCGGGGGGTGGGCGCAGCTCGTCGCGCTCC GCACAAAGTTTGTTTTCTCCCTCCGGGCGGGTGGGGGAGGGCGCAG AGGGCGCGGGGGGAGGAGAGGGGATCTGACGTCAGGCCGCGAGGT GCTTTCCAGCCGCGAGCTGTCAGGCCGAGTGTCAGGCCGGGCAGGT TTACCCAAGGTCCAGCCTAGCCCCTAGGCACCATGTCGGACAGTGAT CTAGGTGAGGACGAAGGCCTCCTCTCCCTGGCGGGCAAAAGGAAGC GCAGGGGGAACCTGCCCAAGGAGTCGGTGAAGATCCTCCGGGACTG GCTGTACTTGCACCGCTACAACGCCTACCCCTCAGAGCAGGAGAAGC TGAGCCTTTCTGGACAGACCAACCTGTCAGTGCTGCAAATATGTAACT GGTTCATCAATGCCCGGCGGCGGCTTCTCCCAGACATGCTTCGGAAG GATGGCAAAGACCCTAATCAGTTTACCATTTCCCGCCGCGGGGGTAA GGCCTCAGATGTGGCCCTCCCCCGTGGCAGCAGCCCCTCAGTGCTG GCTGTGTCTGTCCCAGCCCCCACCAATGTGCTCTCCCTGTCTGTGTG CTCCATGCCGCTTCACTCAGGCCAGGGGGAAAAGCCAGCAGCCCCTT TCCCACGTGGGGAGCTGGAGTCTCCCAAGCCCCTGGTGACCCCTGGT AGCACACTTACTCTGCTGACCAGGGCTGAGGCTGGAAGCCCCACAGG TGGACTCTTCAACACGCCACCACCCACACCCCCAGAGCAGGACAAAG AGGACTTCAGCAGCTTCCAGCTGCTGGTGGAGGTGGCGCTACAGAGG GCTGCTGAGATGGAGCTTCAGAAGCAGCAGGACCCATCACTCCCATT ACTGCACACTCCCATCCCTTTAGTCTCTGAAAATCCCCAGTAGGCATC TGCCAAGAAGGGTGCTGAAGGCTCCAGCCAGCTGTCCTGGGTTTCCG TTTTGGTTCCCTTTCATACAGAGGGTTTTCTATGGATCACTGCCAAACA TTGGGATCATCTCCTCTGTCCAGAGGTCTTCAACAGGAAGATGCCAGC TGGCACCACTGCACTGTGATGGGGCCCTCTCCTCTGCTGACTCTGC CGTTTCTCCAGGCCTCCGCTCAGTGATGAGACCAAGAGATCGGAGAC AAGCATGGTGCTGCTGCTTCTGCTGCTTCTCCAGAAAATCCCTGGGAC ACCTTTGTTCCAGCCTGGTTTCCTGGGCTGGGCTCAGGAAAGCTGCC AAATTCAGTCCTATGTTGGGTCCAAGCTGCCCCTGTGCTGTTTCTGTC AAGCCAGGTGTGGACATTCCAAGTTCATATGCGTGAACAAAAGAAAAG AGGAACCCAGTGGATGTAACAGAACCGACTCCAGTTGAATGTTTAGAT TTTTGCTAAACTGTTTTCTTTTTCCCTTTTTTGCTGTGGTTTGCATTCAC GGCAGTAGTTAGCCCAGGTGTGGGGAACGAGAGTGCACTGCATGATA GCGTTCTGGTGAGCTGGGAAGGACCCACCACTGCCACTGAGGATTGT TTTGGAAGAAAGGAATATTTTTATCTTGGGGACCAGCTAAGTCTCTGC AGTAGTGTGAAATTCCAAATGGTTGTTTTATCATTGGTTTGGTTTACCA AAAAAAAGGCAGGGAAAAAAAAAAAAAAACAACCGTATGAGCGCATTGG CTTGTCTGCCGCAGGCACAGAAGGGTAGAAAGCCACAGCAGGGGGC AGTCCAGCAGACTCTGACTCAACTTTCTAGGCACCTAGCAGAGAAAGA TAAGATCAAAAGGTGTTTGGTTTTTCTTTTAATTTTTATTGTAGTTTTTTT GGGTGGGTGGGGGAAGTAAACTAGACTGAAGCGATGGATTTTTTTTT CTTTTTTTTCTTTAGTGTTTTTCCCTTTGTTCTTGAACACTTTTTGCCCTG CAGCCTCAGTTTTGAATTCTTTTAGCAACTTGGATTAGAGGGGCCCAT ATGTCAGAAGCTCCCAGCACCTCCTACTTGGGAGAAAAGTGAGCCAT CTGCTGGTCAGGAAGTCCTCCAGAGAGGCAGCTTTTCCCACAATGGT GGCAGGAAACTTTGGGGAAAGCAGGAATGGTGTCCACTGCTGCGGAG GAACTGCCTTCAGAGAAGGTGGGGCTGGAAAAGGGTTAGAAGCCTCC TAGCTGGGATTGTCTTTGTTTCACCTTTCTTTAAATTAGAATTACAGAA GCCCCTGCCCAGTGAACAGATAACGATTGGTCTTATGCTCCTCCCTTT CCCCCATTTTTTCTTTTGCTGTTTTGTTTTTTGTTTTTTGTTTGTTTGTTT GTTTTTTTGAGACAGAGTCATGCTCTGTCACCCGGGCTGGAGTGCAGT GGTGCGATCTCAGCTCACTGTAACCTCCGCCTCCCGGGTTCAAGCAA TTATTTGCCTCAGCCTCCCGAGTAGCTGGGATTATAGGCACCCGCCAC CATGTCTGGCTTTTAGTAGAGACGGGGTTTCACCATCTTGGCCAGGCT GGTCTTGGAACTCCTGACCTCGTGAGCCACCACGCCCAGCCTCTTTT GCTGTTTCATTGCTGACAGTGTTCAACAATATGCCCCATCTTTATATAT CCTAAGAAACACTAATCCTAGGTTATTGCTAGCCAAAATATTTTTGTCC TGAGTAGTGTCACTGGGCCAAAAGATAGATCAGGACGACAGCCTTTA GTTTTCCTGAAATCACCAGGTCAGGCACAAGGAGAAAAGGTTCCTGGA TACTGACTAACTTGGGTGGGTCTAGCCAGGAGAAAGACAGTAACATGT GTTCTGTACTTTCTGGGAAGATCCCTGAAGCCATCACAGAGGCTCCCC AACTTCTGAGTCGCCCATCTGTTGCTGTGGGAGTGTGAACGGATCGC TGAAGGAGAGGGAGCTTTGCTCTCTCTAGGTGGGCAAGTTTCCTGGG CTCTCTGTGTTGCCTCCCTCTGGCTTCTTCCTCCCGTGCCCTCTCCCC GTGTGCCCCAGGGGGATCAGGGATCCTCACCCTCCTGAGGCCCAGT GGGGAAGAATGAACATGGCTTCATCCAGGTTAACTGATGCTGCCATTT GCCCAGCCTCTTCCATCCCAGCCCTGTCAGTGAGCCCAGGTCTGGTG CAACTGCTGCAGGATGCCTGTAGTAGGGAACTCTGGAAGTGTATTGG GCTGAGGTGGGATTTTCCCTCCCCACAGTGCACTGAGCAATGGAGGG TGGTGAGGGAGCCATGCTGCTGAATTCTGGTTGGCATTTCCCCATTAT GTAAAATGGGTGTTGGGTAGGGCAGACTCTGCTTGGGTTTGGTTGT AAGATAAACCTGGAGGAGAAGCACAGTTGTCCCATTGAATTATTTGAG | human TGIF2 encoding nucleic acid |

-continued

| SEQ ID No. | Sequence | Description |
|---|---|---|
| | CAAAAACTACTGTAAATAACTTTTTTGTCTTTTGTCAAATAAAATTTTTTT<br>TTGTTTTTTTAAGCAGAAACAAAAAAAAAAAA | |
| 3 | MSDSDLGEDEGLLSLTGKRKRRGNLPKESVKILRDWLYLHRYNAYPSEQ<br>EKLSLSGQTNLSVLQICNWFINARRRLLPDMLRKDGKDPNQFTISRRGGK<br>ASDVALPRGSSPSLLAVSVPAPTNMLSLSVCSMPLHSGQGEKPAAPFPQ<br>VELESPKALVTPASTLTLLTRAEAGSPTGGLFNTPPPTPPEQDKDDFSSF<br>QLLVEVALQRAAEMELQKQQEPAPPLLHTPLPFVSENAK | mouse<br>TGIF2<br>protein |
| 4 | CCACGCTCTGCACAAAGTTTGTTTCTGCCTCGGGGCGGTGGGGGAGG<br>GTGCGGCAGGCGGGATGGGAGGAGAGGGGATCTGACGTCAGGTCGC<br>GAGGTGCTTTCCAGCCGCGAGCTGTCAGGCGGGTGTCAGACCCGGC<br>AGGTACGCGGCGCGTTCCCCCGGTGCCCCCCGCCCCGGCCGGGTG<br>GTCCCACACCCCACCGAGGCCGCGTGGGCCGGAAAGCCGCCAGGGA<br>AGGCTCCCCAGAGGTCCAGCTTAGCCCCTAAGCATCATGTCGGACAG<br>CGATCTAGGCGAGGATGAGGGGCTCCTGTCACTGACCGGCAAGAGG<br>AAGCGCAGAGGGAACCTGCCCAAGGAGTCAGTAAAGATCCTCCGGGA<br>CTGGCTCTATCTGCACCGCTACAACGCCTACCCCTCAGAGCAGGAGA<br>AGCTAAGTCTCTCTGGACAGACCAACCTCTCGGTGCTGCAGATATGTA<br>ACTGGTTCATCAATGCCCGTCGTCGCCTTCTCCCTGACATGCTTCGGA<br>AGGATGGCAAAGACCCTAATCAGTTCACCATCTCCCGTCGTGGGGGT<br>AAGGCCTCTGATGTGGCTCTCCCCAGGGGCAGCAGCCCCTCTCTGCT<br>GGCTGTGTCTGTTCCAGCCCCCACTAACATGCTCTCCTTGTCTGTGTG<br>CTCCATGCCACTCCACTCAGGCCAAGGTGAAAAGCCAGCAGCACCCT<br>TCCCACAAGTGGAGCTGGAATCCCCCAAGGCCCTGGTGACCCCTGCT<br>AGCACACTCACCCTGCTGACTAGGGCAGAGGCTGGAAGCCCCACGG<br>GTGGACTCTTCAATACGCCACCCACCCACACCCCCAGAGCAGGACAAG<br>GATGACTTCAGCAGCTTCCAGTTGCTGGTGGAGGTGGCGCTGCAGAG<br>GGCTGCCGAGATGGAGCTTCAGAAGCAGCAAGAGCCAGCGCCACCTT<br>TGCTACACACTCCGCTGCCTTTCGTCTCAGAAAACGCCAAGTAGGCAC<br>CTGCTCCCGGGTGGCTTGAGGTTCCTGGCTCACTGCCCTTTCATGCA<br>GAGGGTTATCCAAGTACGGATCACTGCCAAGCATCAGGACCATTCTGT<br>CCAGTCCTCAGCGGATGTCGCTGCGCTGCACTGTTACGGGGCCTGTA<br>CTCTGCTGAGTGCCATTCCTTCAAGCGTCCTCTCCGAGGAGACCAAG<br>GCACCAGAGCCAGGCATGGTGTTGCTGCTGCTCCTCCAGAGAGCCCT<br>GGGACACCTGCACTCCAGCCTGCTTTCCTAGGCAGGCTCAGGAAAGC<br>TGCCAAGTCCAGACTTGAGCTGGGTCCAAGCCGCCCCTAAGCTGTGC<br>CTCTTTTGGTCGAGCCAGGTGTGCACATTCCAACCTATTCAAAGGACA<br>AAGGAAATGCCCAGCAGATGTCACAGAACCGACTCCAGTTGAATGTTT<br>AGATTTTTGCTAAATTGTTTTATTTTCCTTTTGCTGTGGTTTGTGTTAAT<br>GCAGTAGGTAGCCCAGAAGCACAGGTGTGGGGAGAGAGCACCTTACA<br>CGGTGGGTGGAGCTCGGTAAGTGGGTAATCTACTTCCCACAGGATGG<br>TTGTATAGGGACCAGCAGATTCTCTGCAGTGGTGCTGAGTTCAGACTA<br>GAGTGGTTGTTTAATTCTTGGTTTGGTCTTCCCTATTATAAAAGACAGA<br>AGGAAAATATCCACAGGTGGTGGGTTATTTGCACCAGACGGTCATTTA<br>GACACAGCAGAGACAGATGACAAAACCAGAGGCACACGTGTTTCTATT<br>GTCGTGGTTAAGCTAGAGTGAAACAGCTCTGTTTTTCTCTCTGTTCTGA<br>GTAACTCCCCTCACCCCACCCCAGCGACCCCCACCCTGCACCACCTT<br>TGTAGCTTGTTTCGGATTTATTCTGGAGCTTGGCAAGAATGTCGTGTG<br>CCAGCATCTACTTGGGAGGAGTGAGCCATCTGCTGGTCATTAGGCCC<br>TTCGGAAAGCTGCTTGTTCACAGAGGCAGCTGGAACCTTCCTGGAGG<br>AGAGGCTGCTGAGGCTACCGACTGGCCCACCTCCCTTCAGGGTGGG<br>ATTGCAAGGGCCTGCCTAAATTTCCCGGGGAAACAGACCACACTTGG<br>TCTTAATCTCTCCCCTTTTCCCGTTTACTTTGCTTAGTTTTCAGCAACA<br>GTATACCCCATCTTTATATCCTAAGAAACACTAATCCTAGATTTGTATTA<br>ACCAAAATACTTGTGTTCTGAATAACCAGAAGATGTGAGGAGCCCTGA<br>CTGTGGTCTGAGGTTCACCCGGGTGTGAGCACAGACGGGGCTCTTGG<br>ATGTTGACTGGCTTGGAGTGCCTGTTCCGAGGAAGGCAGAGACCACT<br>CTGGCCTTTCCAGGGAGCCCCTGAGGCTTAGCAGGCTTCCATACCTC<br>TCCTGAGTGACTTCACCCATCCCTTGCTGTGCAAGTGGGCGCGAGAA<br>TGGCTATTTGTAAGGGGCTGCTTCCCTGGGCTCTGCCTCATGCCTCC<br>CTCTGGCTTCCTGTCCTGTAGGAGACCCAGCAGGCTCAACTCTCTGTC<br>ACCCTGAGGCACTGCTGGGAAGGGAACATGGCTTCATTGACTTTGTG<br>GTTTGCCCACTGCTACCCCACCTGTCTGTGAGACCCCATGATGGCTGT<br>AGGATGCTAAGGCGGGGGTGATACTAGGATGAGGGATTTCTTTTCCC<br>CCCACAGTGCACTGAGCAAGGGAGGAGGGAGGGAGCCATGCTGCTG<br>ACATATTCTGGCATTCCCCTCCTGGGATAAAACAGGGCATCAGAAAG<br>GTAGAGCGGTCTCTGCTTAGGTTGCCTGTAAGATAAATGTGGAGAAGC<br>ACGGTTGTCCCATTGAACAATATTTGAGCAAAAACTACTGTAAATAAC<br>TGGTTTTTGTCTTTTGTCAAATAAAATTGTTTTGGTTTTGTTTATGTTTTA<br>AAGTCAAA | mouse<br>TGIF2<br>encoding<br>nucleic acid |

The "Liver-Specific" or "Pancreas-Specific" Markers as Used Herein Relate to Molecular markers that are repressed or expressed, respectively, primarily in these cell types. Expression of such markers may exist to some extent in other cell types, although primarily, these markers may be used to differentiate between the hepatic and pancreatic lineages. The absolute absence of a repressed marker is not required for "repression" according to the present invention.

It is possible that low levels remain present in the cell. Repression of liver-specific markers may be characterised as reduced levels of expression compared to liver cells. Reduced levels compared to an appropriate control may be used for determining "repression". Similarly, "activation" of gene expression of pancreas-specific genes can be determined by comparison to an appropriate control, such as liver cells. A repression constitutes in some embodiments, for example a reduction of the marker by at least 20%, 30%, 40%, 50%, 60%, 70%, 80% or 90% relative to a control, such as a liver cell. An activation constitutes in some embodiments, for example an increase of expression by at least 30%, 40%, 50%, 60%, 70%, 80%, 90%, 100%, 150% or 200% relative to a control, such as a liver cell. Diabetes mellitus (DM), also known as simply diabetes, is a group of metabolic diseases in which there are high blood sugar levels over a prolonged period. A high blood sugar level in a subject refers to a fasting blood glucose concentration of, e.g., greater than 7 mmol/L, greater than 8 mmol/L, greater than 9 mmol/L, greater than 10 mmol/L or greater than 11 mmol/L (see U.S. Pat. No. 9,078,866 which is incorporated herein by reference in its entirety). This high blood sugar produces the symptoms of frequent urination, increased thirst, and increased hunger. Untreated, diabetes can cause many complications. Acute complications include diabetic ketoacidosis and nonketotic hyperosmolar coma. Serious long-term complications include heart disease, stroke, kidney failure, foot ulcers and damage to the eyes. Diabetes is due to either the pancreas not producing enough insulin, or the cells of the body not responding properly to the insulin produced. There are three main types of diabetes mellitus; namely Type 1 DM results from the body's failure to produce enough insulin. This form was previously referred to as "insulin-dependent diabetes mellitus" (IDDM) or "juvenile diabetes". Type 2 DM begins with insulin resistance, a condition in which cells fail to respond to insulin properly. As the disease progresses a failure of beta-cells and consequent lack of insulin production may also develop. Gestational diabetes, is the third main form and occurs when pregnant women without a previous history of diabetes develop a high blood glucose level.

The invention therefore relates to cells and vectors for the treatment of DM. The invention also encompasses methods of treatment of a subject that has, or is at risk of having, DM. One example of a subject at risk is a pre-diabetic subject. As used herein, a "prediabetic" subject includes, without limitation, a subject who has the complex of symptoms that indicate he will likely develop diabetes. Prediabetic subjects generally have higher-than-normal insulin levels. Normal levels of insulin range between above 63 mg/dL and below and 126 mg/dL. Levels below/above those values are considered to constitute hypoglycemia and hyperglycemia, respectively.

As used herein, "treating" a subject with DM shall mean slowing, stopping or reversing the progression, or reducing the risk of having DM. In a preferred embodiment, treating a subject afflicted with DM means reversing the disorder's progression, ideally to the point of eliminating the disorder itself. As used herein, ameliorating a disorder and treating a disorder are equivalent.

As used herein, cellular therapy comprises introducing or administering said therapeutic cells into a subject.

In a preferred embodiment, during DM-cellular therapy, systemic (blood stream) administration of the cells is initially avoided and administration is conducted in a local manner. For example, in the Edmonton protocol the pancreatic islet transplantation is conducted into the portal vein of the liver. Such a method and similar methods of administration are encompassed in the present invention. The present invention therefore encompasses the local administration of the cells as described herein, in particular via injection, infusion or via catheter into the liver, in particular into the portal vein of the liver.

Although local administration is preferred, in one embodiment of the invention the administration may be carried out via intravenous administration, or by introducing the cells into a subject's blood stream. The term "introducing" cells "into the subject's bloodstream" shall include, without limitation, introducing such cells into one of the subject's veins or arteries via injection.

Administering can also be performed, for example, once, a plurality of times, and/or over one or more extended periods. A single injection is preferred, but repeated injections over time (e.g., quarterly, half-yearly or yearly) may be necessary in some instances. Such administering is also preferably performed using a mixture of therapeutic cells and a pharmaceutically acceptable carrier.

Pharmaceutically acceptable carriers suitable for cellular administration are well known to those skilled in the art and include, but are not limited to, 0.01-0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as Ringers dextrose, those based on Ringers dextrose, and the like. Fluids used commonly for i.v. administration are found, for example, in Remington: The Science and Practice of Pharmacy, 20th Ed., p. 808, Lippincott Williams S-Wilkins (2000). Preservatives and other additives may also be present, such as, for example, antimicrobials, antioxidants, chelating agents, inert gases, and the like.

As used herein, "subject" shall mean any animal, preferably a human, non-human primate, mouse, rat, guinea pig or rabbit.

The invention also relates in one embodiment to the administration of a therapeutically effective number of pancreatic progenitor cells as described herein. As used herein, a "therapeutically effective number" of cells includes, without limitation, the following amounts and ranges of amounts: (i) from about $1 \times 10^2$ to about $1 \times 10^8$ cells/kg body weight; (ii) from about $1 \times 10^3$ to about $1 \times 10^7$ cells/kg body weight; (iii) from about $1 \times 10^4$ to about $1 \times 10^6$ cells/kg body weight; (iv) from about $1 \times 10^4$ to about $1 \times 10^5$ cells/kg body weight; (v) from about $1 \times 10^5$ to about $1 \times 10^6$ cells/kg body weight; (vi) from about $5 \times 10^4$ to about $0.5 \times 10^5$ cells/kg body weight; (vii) about $1 \times 10^3$ cells/kg body weight; (viii) about $1 \times 10^4$ cells/kg body weight; (ix) about $5 \times 10^4$ cells/kg body weight; (x) about $1 \times 10^5$ cells/kg body weight; (xi) about $5 \times 10^5$ cells/kg body weight; (xii) about $1 \times 10^6$ cells/kg body weight; and (xiii) about $1 \times 10^7$ cells/kg body weight. Human body weights envisioned include, without limitation, about 50 kg, about 60 kg; about 70 kg; about 80 kg, about 90 kg; and about 100 kg.

The invention encompasses further the administration of expression vectors to a subject in need thereof. A "vector" is any means for the transfer of a nucleic acid into a host cell.

A preferred vector relates to a replicon to which another DNA segment may be attached so as to bring about the replication of the attached segment. The term "vector" as used herein specifically refers to means for introducing the nucleic acid into a cell in vitro, ex vivo or in vivo. Viral vectors include, without limitation, retrovirus, adeno-associated virus, pox, baculovirus, vaccinia, herpes simplex, Epstein-Barr and adenovirus vectors.

Non-integrating viral systems, such as adeno-associated viral vectors (AAV), represent a preferred embodiment for the gene therapy approaches described herein due to a number of advantageous benefits (see Asokan et al., Molecular Therapy vol. 20 no. 4, 699-708). For example, AAV are of particular interest in gene therapy due to their very limited capacity to induce immune responses in humans, a factor which positively influences vector transduction efficiency while reducing the risk of any immune-associated pathology. The AAV genome is typically built of single-stranded deoxyribonucleic acid (ssDNA), either positive- or negative-sensed, which is about 4.7 kilobases long. The AAV genome comprises inverted terminal repeats (ITRs) at both ends of the DNA strand, and two open reading frames (ORFs): rep and cap. Development of AAVs as gene therapy vectors has eliminated the integrative capacity of the vector by removal of the rep and cap from the DNA of the vector. Any given desired gene, together with a promoter to drive transcription of the gene (for example the inventive TGIF2 as described herein), is inserted between the inverted terminal repeats (ITR) that aid concatemer formation in the nucleus after the single-stranded vector DNA is converted by host cell DNA polymerase complexes into double-stranded DNA. AAV-based gene therapy vectors typically form episomal concatemers in the host cell nucleus. In non-dividing cells, these concatemers remain intact for the life of the host cell. In dividing cells, AAV DNA is lost through cell division, since the episomal DNA is not replicated along with the host cell DNA.

The vector of the present invention may be administered as a formulation. A "formulation" refers to an aqueous or solution medium for the preservation and/or administration of expression vectors, preferably of viral particles and viral vectors, which is directly injectable into an organism. It relates more particularly to a formulation for a recombinant adenovirus vector that optimally enhances the vector titer, or stabilizes the vector at refrigerator or room temperature, or both, for example in an aqueous buffer. The aqueous buffer may include salts or sugars, or both, at about an isotonic concentration, preferably with a pharmaceutically acceptable carrier. The phrase "pharmaceutically acceptable" refers to molecular entities, at particular concentrations, and compositions that are physiologically tolerable and do not typically produce an allergic or similar untoward reaction, such as gastric upset, fever, dizziness and the like, when administered to a human or non-human animal.

The use of a formulation according to the invention makes it possible to preserve viral particles and viral vectors and to administer it directly into a subject, without a centrifugation or washing stage, with a good viability and/or without affecting its capacity to infect a susceptible cell of the organism. To this end, the present invention also relates to preparations and compositions containing the formulation according to the invention and viral particles or viral vectors.

As regards viruses, these are preferably previously purified (e.g., by centrifugation on a cesium chloride gradient, column chromatography, plaque purification, and the like). They may be packaged at the rate of $10^4$ to $10^{15}$ particles per ml, preferably $10^5$ to $10^{12}$.

According to the invention, the formulation or composition of the invention may be introduced parenterally or transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration.

DETAILED DESCRIPTION OF THE FIGURES

FIG. 1. TGIF2 controls pancreatic and hepatic cell lineage divergence in foregut progenitors. a, RT-qPCR analysis of Tgif2 expression in the mouse foregut (fg) endoderm and its derivatives, liver and pancreas. Data were normalized to that of SDHA and represented as fold change compared to liver samples (set to 1 as calibrator). E8.5 fg was compared to E10.5 liver sample. Error bars represent ±SEM. (*) p<0.05. b, Immunofluorescence analysis of TGIF2 in mouse embryos. TGIF2 colocalizes with FOXA2 in the E7.5 anterior definitive endoderm and with PROX1 in the E8.5 prospective pancreatic endoderm at the foregut lip (see arrowhead). Arrow indicates prospective hepatic endoderm. Inset panels depict TGIF2 single channel image of the area in the dashed box. Embryos are presented in lateral view. Abbreviations: ht, heart; vpa, ventral pancreas. Scale bars, 50 µm. c, Whole-mount in situ hybridization detects Tgif2 in lateral domains of the ventral foregut (see arrows) of early somite stage (S) mouse embryos. Embryo is presented in ventral view. d, In situ hybridization analysis on mouse cryosections detects expression of Tgif2 in the whole pancreatic epithelium (demarcated by black line) at E12.5. Abbreviations: pa, pancreas; st, stomach. Scale bar, 50 µm. e, Directed differentiation of mESC monolayer cultures into definitive endoderm (DE) and pancreas endoderm (PE). RT-qPCR analysis of endodermal and pancreatic gene expression on day (d) 8 of differentiation of PE transduced with LV-TGIF2 (see FIG. 2) and control non-transduced PE. Induction of endogenous Tgif2 transcript was observed during directed differentiation of ESCs toward endoderm, consistent with its expression profile in the gastrulating mouse embryo (FIG. 1b). Data were normalized to that of SDHA and shown as Log 2-expression ratio relative to control undifferentiated ES cultures. Error bars represent ±SEM. (*) p<0.05.

Figure 2:
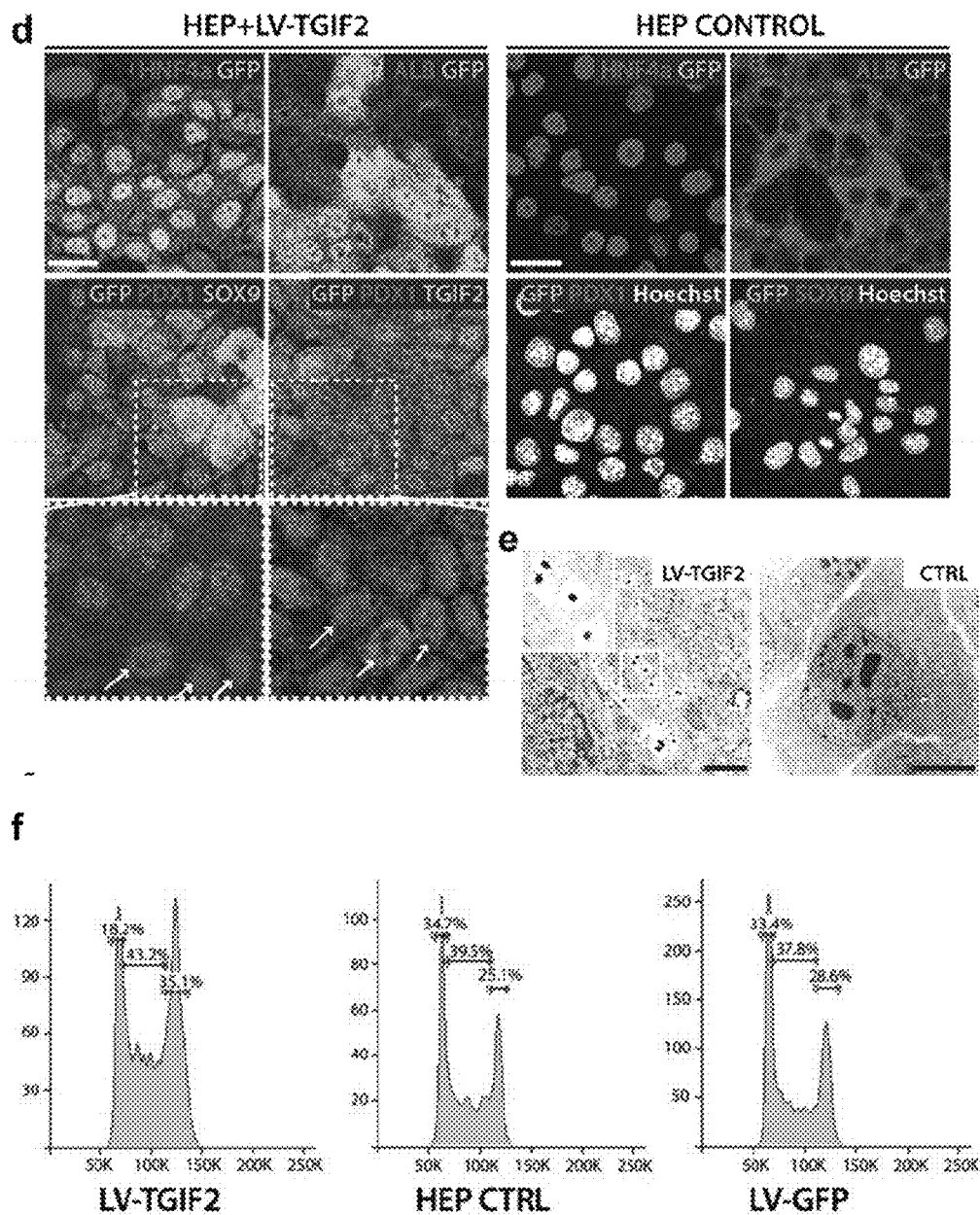
FIG. 2

FIG. 2. Tgif2 expression induces adult murine liver cells to acquire molecular features of pancreatic progenitors. a, Map of lentiviral vectors (LV) and schematic of the ex vivo experimental approach. Murine adult hepatic (HEP) cells were transduced with the constitutively active PGK-TGIF2-EGFP LV (LV-TGIF2) expressing Tgif2 and EGFP. Transduced cells were FACS-sorted for EGFP and characterized at different time points by various ex vivo and in vivo approaches. b, RT-qPCR analysis of hepatic and pancreatic gene expression in primary hepatocytes (primary HEP) at 7 d and 14 d after transduction with LV-TGIF2. c, RT-qPCR analysis of hepatic and pancreatic gene expression in murine adult BAML hepatic cells (HEP) transduced with LV-TGIF2 at the indicated time points after transduction. Data were normalized to SDHA and represented as Log 2-expression ratio between LV-TGIF2-transduced and control cells. Error bars represent ±SEM. (*) p<0.05. d, Immunofluorescence staining of LV-TGIF2-transduced HEP and control cells. In insets, examples of either PDX1/SOX9- or PDX1/TGIF2- double positive cells (arrows). Scale bar, 50 µm. e, Transmission electron microscopy (TEM) of HEP+LV-TGIF2 (scale bar, 1 µm) and HEP control (CTRL) cells (scale bar, 10 µm). Inset shows high magnification of the outlined areas, containing typical immature insulin secretory granules with paracrystalline electron-dense core surrounded by an external electron-lucent halo. No granules with characteristics of the α-cell granule type or zymogen granules, typical of exocrine differentiation, were detected. f, Flow cytometric analysis of cell cycle using propidium iodide (PI) DNA staining of HEP cells at day 4 after transduction with LV-TGIF2 or LV-GFP and non-transduced HEP control (CTRL). The x-axis shows fluorescence intensity (PI) and y-axis represents cell count. % of cells in each cell cycle phase is indicated. All experiments were repeated at least three times and data shown are representative.

Figure 3:
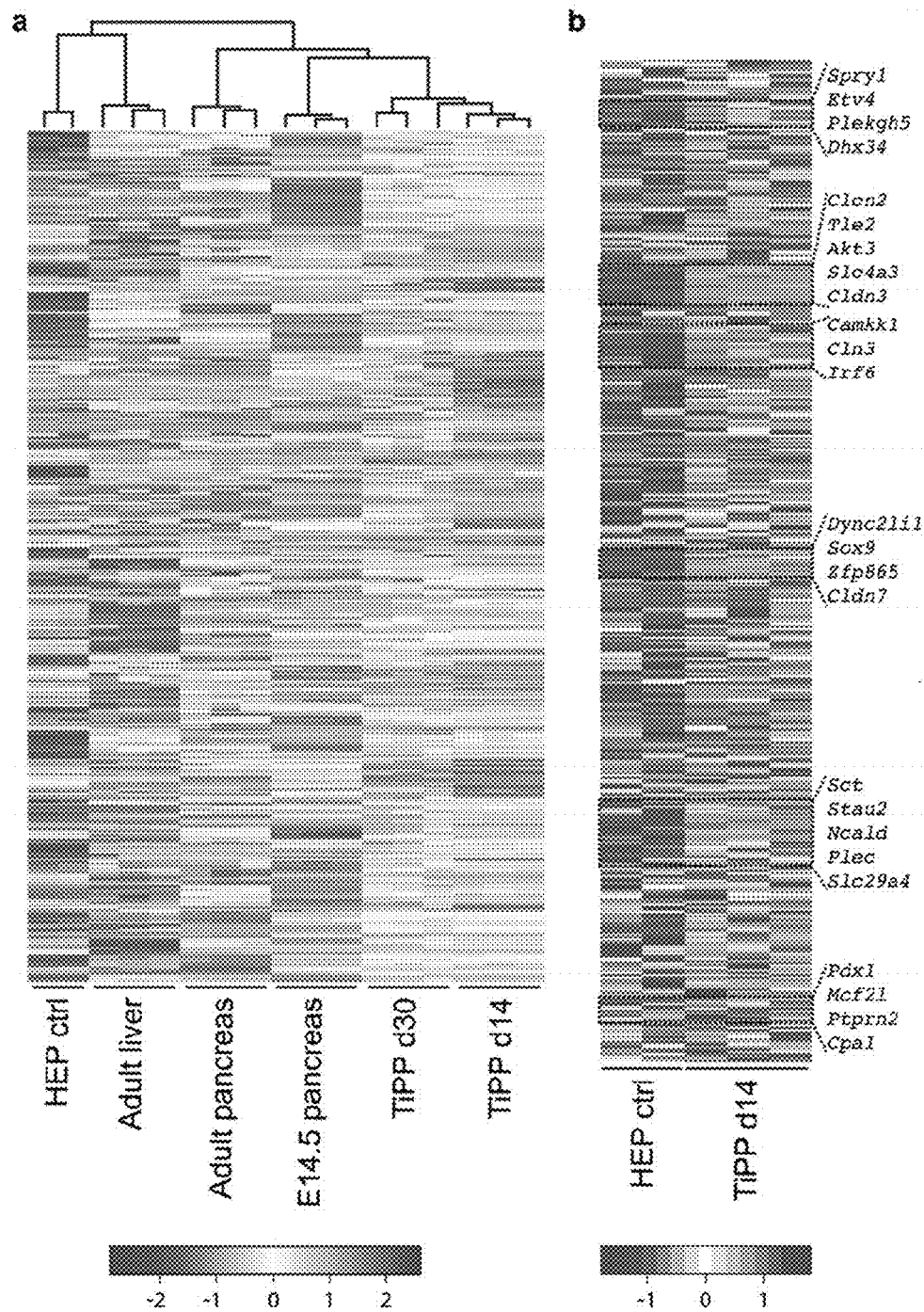
FIG. 3. Lineage conversion is accompanied by global transcriptional remodeling.
Figure 3:
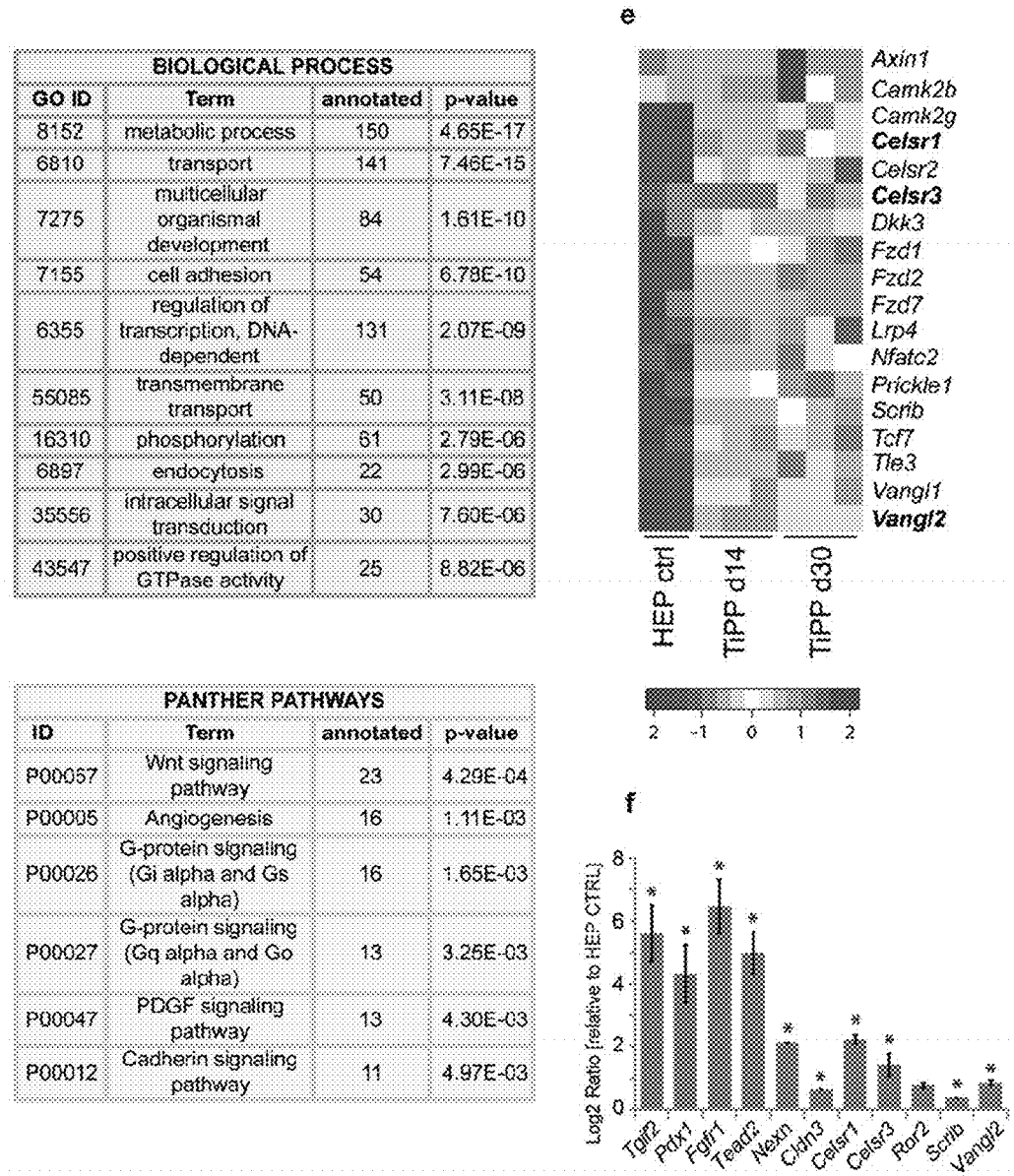

FIG. 3. Lineage conversion is accompanied by global transcriptional remodeling. a, Hierarchical clustering of the gene expression values of the sub-set of genes that were differentially expressed between HEP control and TiPP cells at d14 (total 592 genes; p-value<0.01 and FC>4 or <−4) among all samples analyzed. Values in the heat maps represent high or low expression levels, respectively. Values were scaled per row to have mean zero and standard deviation one. b, Heat map of pancreatic progenitor signature genes in HEP control and TiPP cells at d14 (TiPP-dl 4 versus control population; p-value<0.05). A total of 296 genes were defined as pancreatic progenitor-specific signature genes for their high expression values (FPKM>10) in mouse E10.5 pancreatic progenitors and low expression values (FPKM<10) in E10.5 hepatic progenitors in RNA-Seq datasets (reference 24). c, GO "biological process" annotation enrichment analysis performed on the list of differentially regulated genes in HEP control and TiPP cells at d14 (p-value<0.05 and FC>2 or <−2). Complete analysis is shown in Supplementary Table 1. d, Panther pathways annotation enrichment analysis performed on the list of differentially regulated genes in HEP control and TiPP cells at d14 (p-value<0.05 and FC>2 or <−2). e, Heat map illustrating the relative expression levels of selected Wnt signaling pathway genes. Genes in bold were selected for confirmation by RT-qPCR analysis. f, Confirmation of microarray gene expression changes by RT-qPCR analysis. Data were normalized to SDHA and are represented as Log 2-expression ratio between TiPP cells at d14 and HEP control cells. Error bars represent ±SEM. (*) p<0.05.

Figure 4:
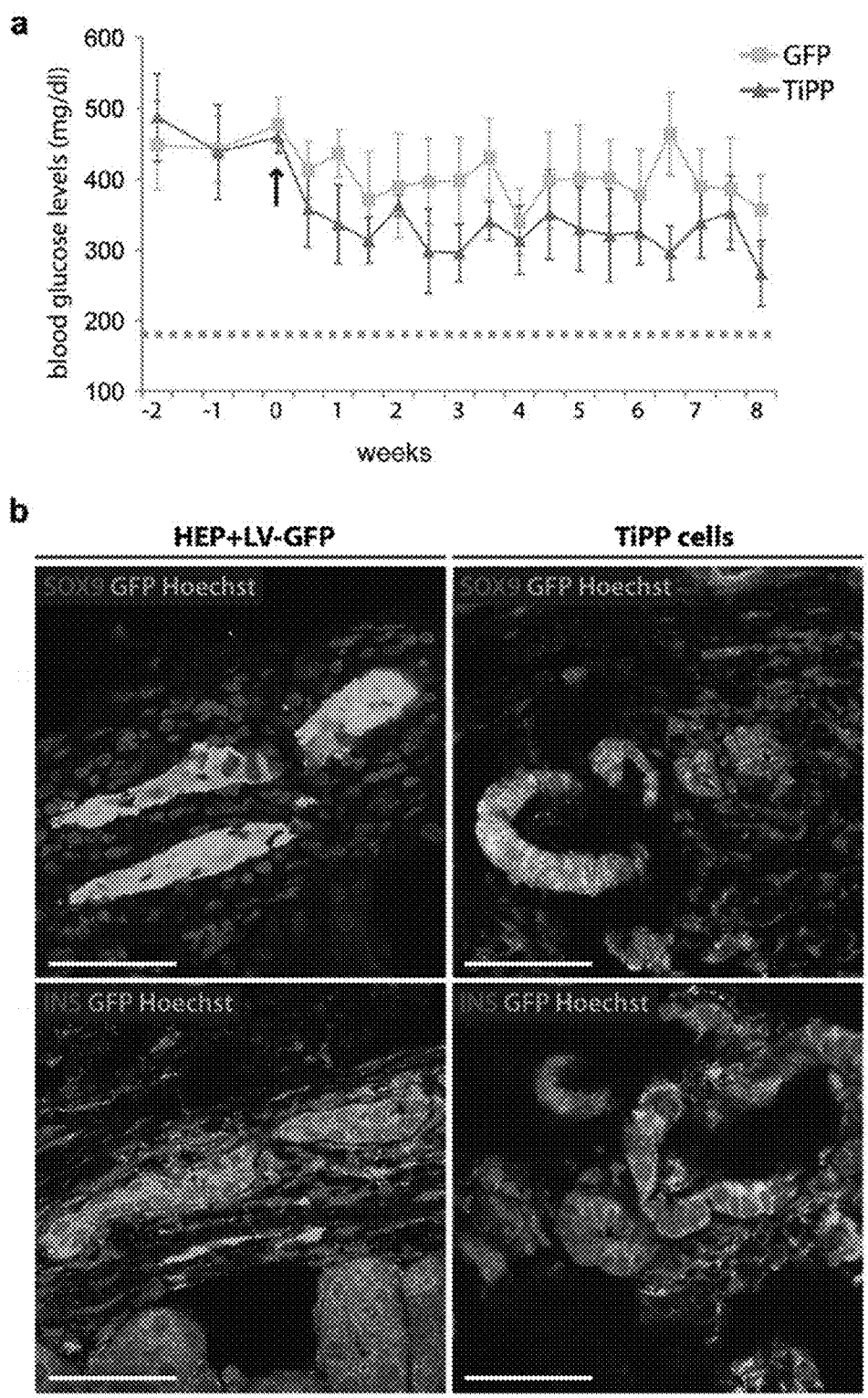
FIG. 4. In vivo analysis of TGIF2 reprogramming activity.
Figure 4:
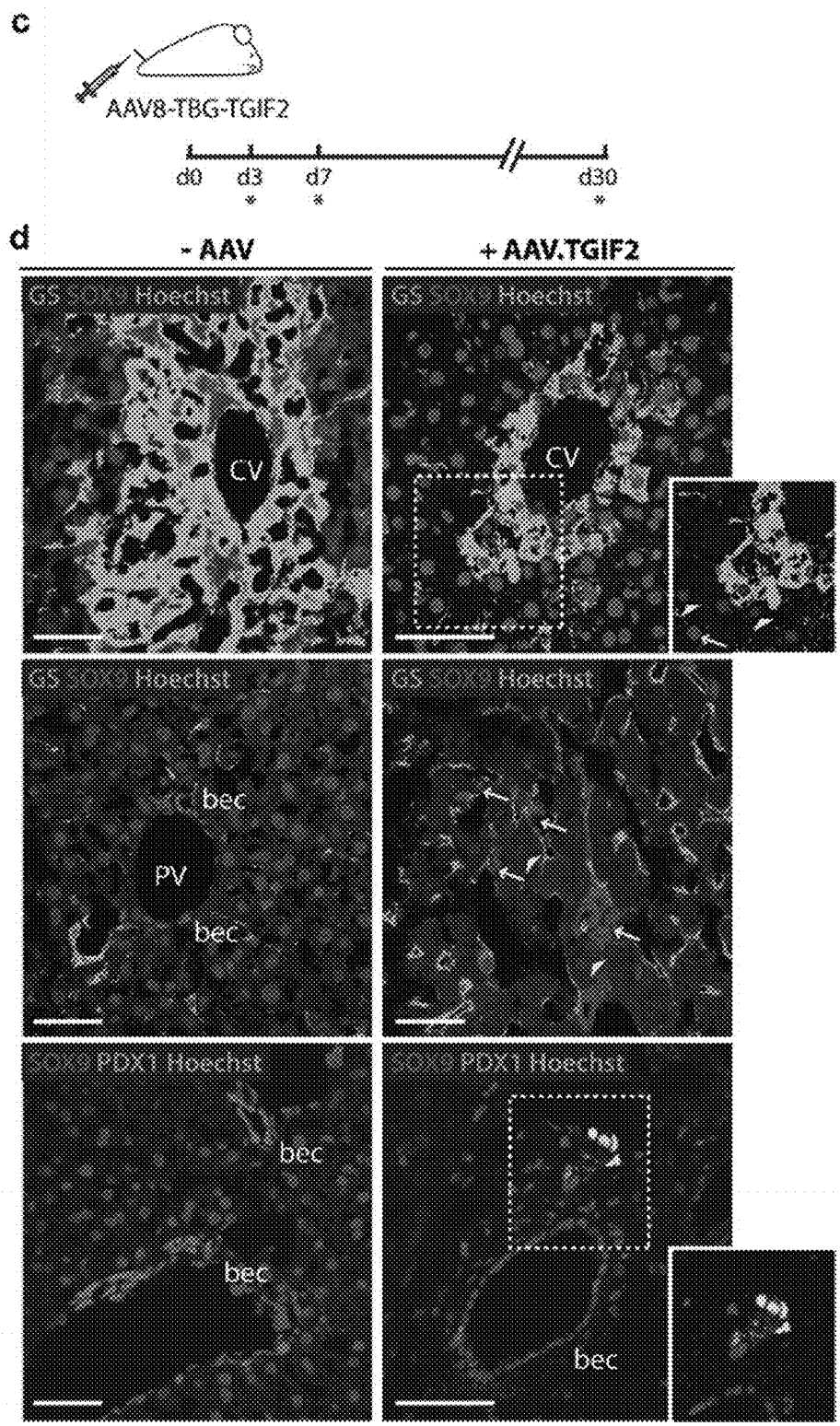

FIG. 4. In vivo analysis of TGIF2 reprogramming activity. a, Transplantation assays in the Akita diabetic mice. Reprogrammed TiPP cells (d8 post-transduction) were grafted under the kidney capsules of hyperglycemic Akita mice (red line). Animals engrafted with HEP cells transduced with LV-GFP were used as negative controls (green line). Blood glucose levels were measured under non-fasting conditions before transplantation (time points: −2 wk and −1 wk), the day of transplantation (time point 0; see arrow) and, subsequently, twice a week after transplantation. n=6 in each group. Normoglycemia was defined as blood glucose level below 200 mg/dl in wild-type littermate mice under non-fasting conditions (dotted line). Error bars represent ±SEM. p<0.01 (two-way ANOVA comparison test between LV-GFP and TiPP transplanted groups). b, Immunofluorescence analysis on cryosections of mouse kidneys transplanted with LV-GFP HEP cells and TiPP cells. Scale bars, 50 µm. c, Schematic of the AAV-mediated experimental strategy to express Tgif2 in vivo in the adult mouse liver. AAV-injected and uninjected control livers were examined at the indicated time points (*) after iv injection. n=2 at d3; n=4 at d7; n=4 at d30. d, Immunofluorescence staining of AAV-injected (+AAV.TGIF2) and uninjected (−AAV) adult mouse livers for Glutamine synthethase (GS), SOX9 and PDX1. SOX9 marks biliary epithelial cells (see bec) in control adult liver, but it is not expressed in hepatocytes. Importantly, AAV injection itself (e.g. AAV-GFP or AAV.Cre) did not induce activation of SOX9 in the liver parenchyma (data not shown). Arrows indicate examples of cells with high SOX9; arrowheads indicate examples of cells with low SOX9. Outlined areas are shown in the insets without nuclear counterstaining (blue filter). bec, biliary epithelial cells; CV, central vein; PV, portal vein. Scale bars, 50 µm.

Figure 5:
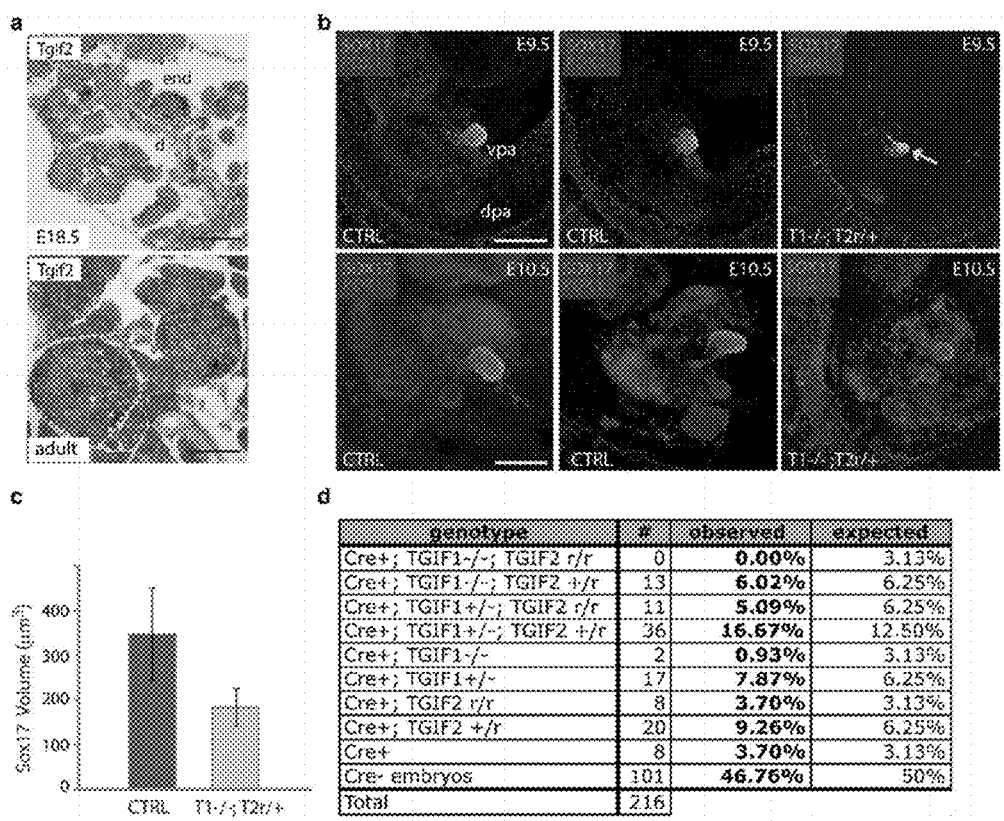
FIG. 5. The TALE Tgif gene family is required for proper lineage segregation within the ventral foregut endoderm of the mouse embryo.

FIG. 5. The TALE Tgif gene family is required for proper lineage segregation within the ventral foregut endoderm of the mouse embryo. a, In situ hybridization analysis for Tgif2 on cryosections of mouse pancreas at E18.5 and after birth. At birth and in adults, Tgif2 expression was maintained in the pancreas, becoming restricted to the duct and endocrine compartments. Endocrine islets are demarcated by yellow dotted lines. Abbreviations: d, ducts; end, endocrine. Scale bars, 100 l&m. b, Representative maximum confocal z-projections of PDX1 and SOX17 immunofluorescence analysis in control (CTRL) and Tgif1−/−; Tgif2lox/+; Sox2-Cre+; (referred to as T1−/−; T2r/+) mouse embryos. PDX1 marked both dorsal and ventral pancreatic buds and at E9.5 co-localized with SOX17 in the pancreatobiliary progenitor population that gives rise to the ventral pancreas, extrahepatic ducts, and gall bladder34, 35,37 (see arrows). Abbreviations: dpa, dorsal pancreas; r, recombined; vpa, ventral pancreas. Scale bars, 50 l&m. c, Quantification of the volume of SOX17+ buds from confocal images of E9.5 embryos. Average fluorescence intensity was measured in SOX17+ buds using the "object analysis" function in Huygens software. Error bars indicate ±SEM. n=6. d, Table summarizing the observed and expected frequency of genotypes (%) of 216 embryos obtained from breeding of Tgif1+/−; Tgif2lox/+; Sox2-Cre+X Tgif1+/−; Tgif2lox/+ mice. Embryos were dissected between embryonic stages E7.5-E12.5. No double null embryos were found at E7.5 in our background. r, recombined.

Figure 6:
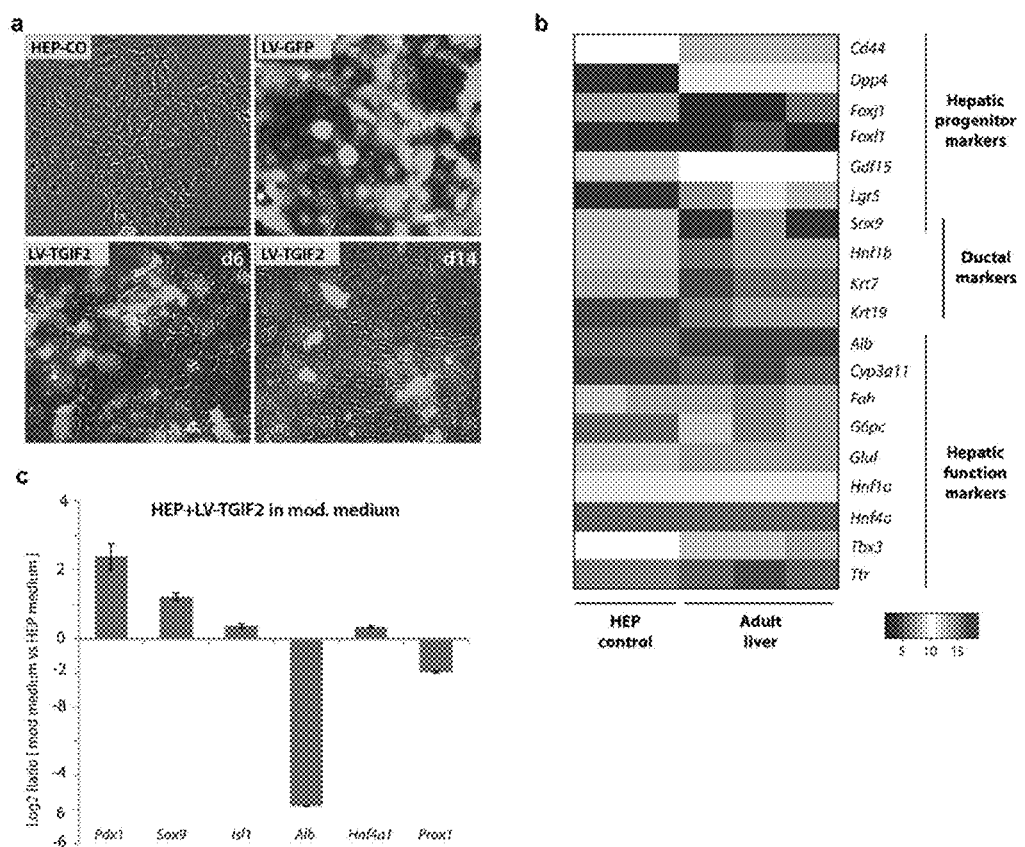
FIG. 6. Characterization of HEP cells expressing Tgif2.

FIG. 6. Characterization of HEP cells expressing Tgif2. a, Transduction efficiency with LV-TGIF2 in primary HEP (not shown) and BMAL cell line was above 80%, as judged by direct visualization of GFP fluorescence and FACS analysis. Bars, 50 µm. b, Heat map of expression levels of selected hepatic progenitor, ductal and hepatic function markers in HEP (BAML) control cells and adult liver tissue. HEP displayed mature hepatic molecular features similar to adult mouse liver and were not enriched for hepatic progenitor markers46. Colors represent high (red) or low (blue) expression levels. c, RT-qPCR analysis of Tgif2-expressing HEP cells upon changes of growth culture conditions. HEP cells were transduced with LV-TGIF2 and cultured for 14 days either in the modified medium, which was depleted of insulin, IGF II and dexamethasone, or in normal conditions. Removal of dexamethasone from the growth medium improved fate conversion of hepatocytes to pancreatic progenitor fate. Data were normalized to that of SDHA and shown as 2-log fold changes compared to cells in complete medium. Error bars represent ±SEM.

Figure 7:
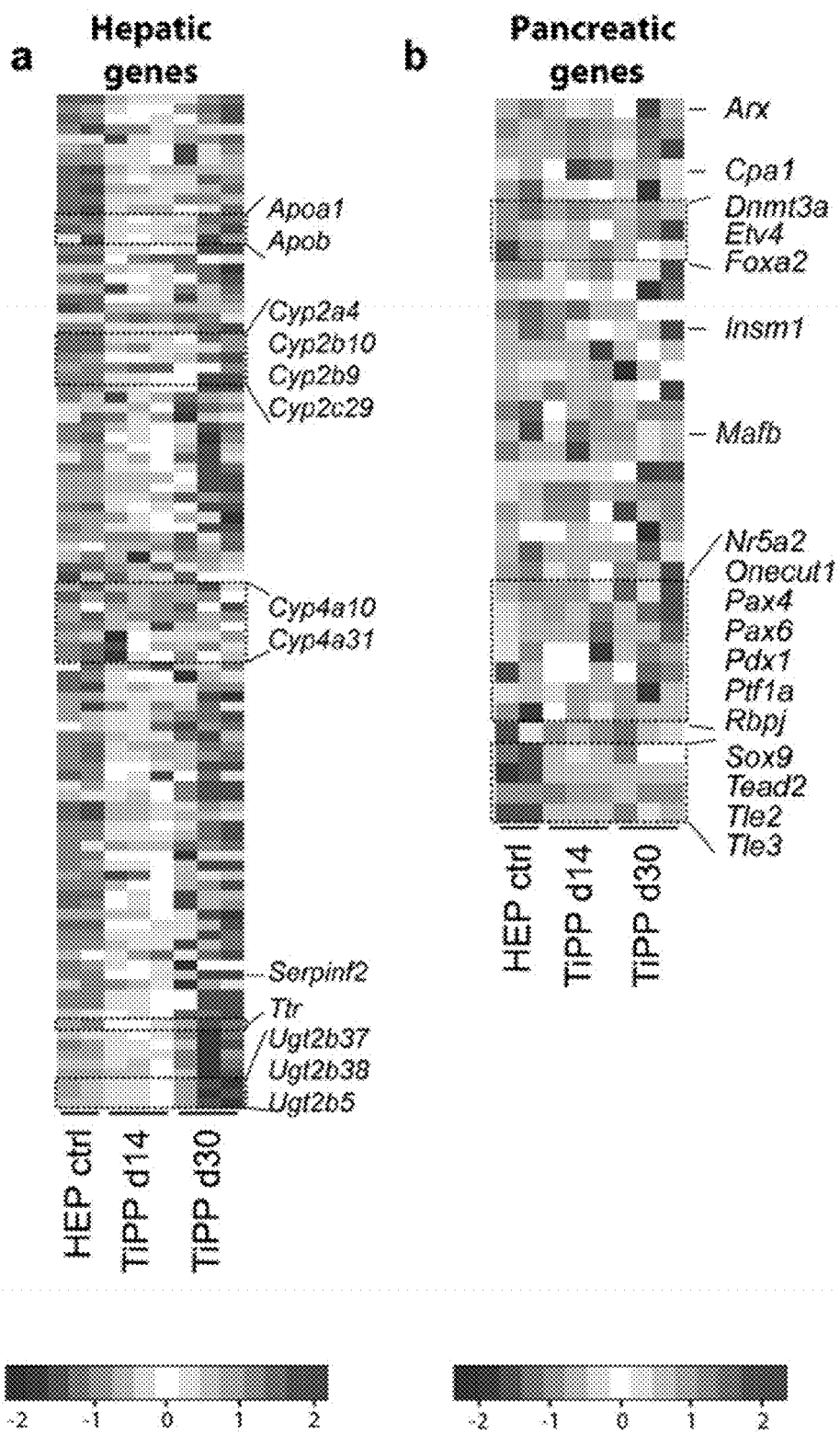
FIG. 7. Global transcriptome analysis of reprogrammed Tgif2-induced pancreatic progenitor (TiPP) cells.

FIG. 7. Global transcriptome analysis of reprogrammed Tgif2-induced pancreatic progenitor (TiPP) cells. a, Heat map illustrating the relative expression levels of selected hepatic genes involved in metabolic activities in HEP control and TiPP cells at d14 and d30. b, Heat map illustrating the relative expression levels of selected pancreatic genes in HEP control and TiPP cells at d14 and d30. Tgif2 induces expression of pancreatic progenitor genes and stably down-regulates hepatic hallmarks in liver cells. Values were scaled per row to have mean zero and standard deviation one.

Figure 8:
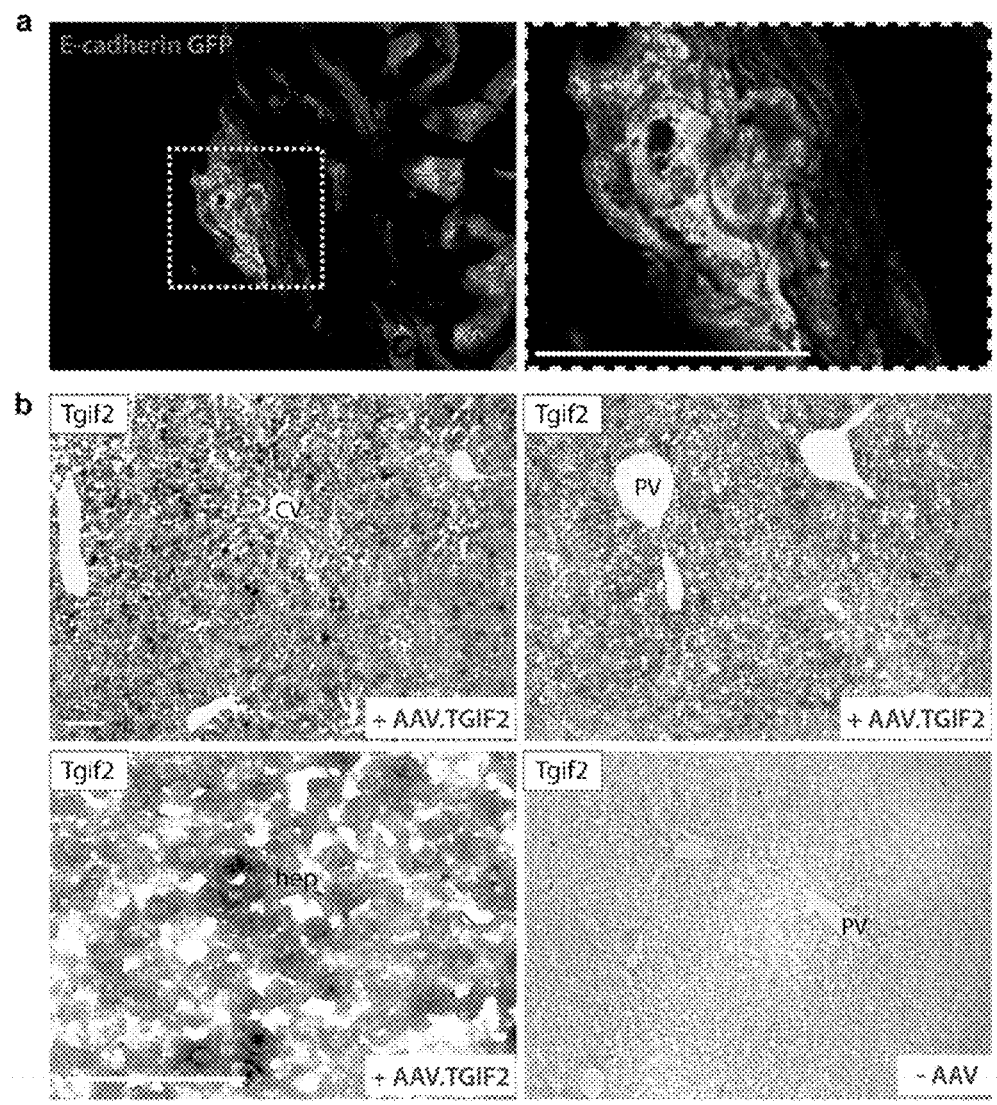
FIG. 8. Characterization of TiPP cells in vivo.

FIG. 8. Characterization of TiPP cells in vivo. a, Immunofluorescence analysis of E-cadherin on cryosections of mouse kidneys transplanted with TiPP cells. The right panel shows a higher magnification of the boxed area. Scale bars, 50 µm. b, In situ hybridization with Tgif2 antisense RNA probe on liver cryosections of control (−AAV) and AAV.T-GIF2-injected adult mice. Robust induction of Tgif2 transcript was observed only in the liver of AAV.TGIF2-injected animals throughout the parenchyma. Scale bars, 100 µm. CV, central vein; hep, hepatocytes; PV, portal vein.

EXAMPLES

The invention is further described by the following examples. The examples represent particular and in some cases preferred embodiments of the invention and are not intended to limit the scope of the invention. The experimental examples relate to evidence that TGIF2 is a novel regulator of pancreas versus liver lineage fate decision in mammalian foregut progenitors and exerts a twofold reprogramming activity: i. it unlocks hepatic cell identity and promotes erasure of hepatic initial identity, and ii. it establishes pancreas cell identity. The experimental examples provided herein are conducted in mouse models. These models are used as a model for mammalian subjects, including humans. The technical effects described herein are applicable for mammals, in particular for human subjects. Genes and names thereof may relate either to mouse or other mammalian genes, in particular human genes, including any analogues/orthologues thereof.

Liver and Pancreas Fate Divergence

The inventors identified the Three-amino-acid-loop-extension (TALE) homeobox transcription regulator TG-interacting factor 2 (TGIF2) as a potential re-programming factor. TGIF2 exhibits a distinct expression signature at the cell-fate branchpoint, being expressed in the common endoderm progenitor pool, and whose expression changes in opposite directions as cells commit to pancreatic or hepatic lineages[24,26] (FIG. 1). The TALE class of homeodomain-containing transcription factors is known to play crucial roles in establishing cell identity and organogenesis, including pancreas formation[27,28,29]. The inventors found that foregut endoderm progenitors expressed elevated Tgif2 levels (reference 24) (FIG. 1a). Importantly, at 2-somite stage (E8.0) Tgif2 expression was spatially confined to the caudo-lateral region of the ventral foregut endoderm, which is the location of presumptive ventral pancreas progenitors (reference 30) (FIG. 1c). Subsequently, by 7-9 somite stage (E8.5), whole-mount immunofluorescence showed co-localization of TGIF2 with the transcription factor PROX1 in ventral pancreatic progenitors at the lip of the foregut but not in hepatoblasts (FIG. 1b). After the fate decision between liver and pancreas is made, Tgif2 exhibited high and persistent expression levels in pancreas throughout embryonic development as well as in adulthood, whereas it was undetectable in the liver (FIG. 1, FIG. 5a).

Because of the early and highly regionalized expression of Tgif2 in ventral foregut progenitors, the inventors investigated whether it regulates the allocation of multipotent foregut progenitor cells to pancreas fate and is sufficient for the activation of pancreatic transcriptional program. Given the high degree of functional overlap between Tgif2 and its closely related family member, Tgif1, during mouse embryogenesis (references 27, 31), the inventors generated conditional deletion of Tgif2 in the epiblast using a loxP-flanked Tgif2 allele (reference 32) in a Tgif1-deficient background (reference 33) (FIG. 5). No double homozygous mutant embryos [Tgif2r/r; Tgif1−/−; Sox2-Cre] were found in the genetic background used, hampering a complete loss-of-function analysis (FIG. 5d). However, the presence of one single wild-type allele of either gene supported normal embryonic development to at least E10.5, enabling the analysis of ventral foregut organogenesis (FIG. 5d). The inventors analyzed the expression of Sox17, a gene involved in the segregation between liver and pancreatobiliary systems, and which is expressed in ventral pancreatic progenitors from E9.5 onward (references 34, 35, 36, 37). Interestingly, mouse embryos with these compound mutations [Tgif2r/+; Tgif1−/−; Sox2-Cre or Tgif2r/r; Tgif1+/−; Sox2-Cre] showed consistent reduction of the SOX17/PDX1 composite ventral pancreatic bud at E9.5 (FIG. 5b, 5c). These results suggest a role for TGIF homeoproteins in lineage divergence within the ventral foregut endoderm.

Next, the inventors directly assayed Tgif2 for pancreatic fate-inducing activity. To model ex-vivo endoderm development and specification of pancreas progenitors, the inventors used a directed stepwise differentiation system of mouse embryonic stem cells (ESC), adapted from previously published studies (references 24, 38, 39). Monolayer cultures of mES cells underwent directed differentiation into definitive endoderm (DE), transduction with a bicistronic lentiviral vector (LV) expressing Tgif2 and the reporter enhanced green fluorescent protein (EGFP) genes, and then differentiation into pancreatic endoderm (PE) (FIGS. 1e and 2a). When overexpressed in ES cells, Tgif2 enhanced differentiation of the DE-induced population toward pancreatic fate, as judged by the further increase in expression levels of Sox17, Foxa2 and Pdx1, but absence of the hepatic gene Albumin (FIG. 1e). Taken together, the results provided herein indicate that TGIF2 acts as a developmental regulator of the hepatopancreatic lineage, pushing foregut progenitors toward pancreatic cell fate.

Stepwise Reprogramming of Liver Cells to Pancreas Progenitors

To assess re-programming, first the inventors developed an ex-vivo lineage reprogramming strategy based on a lentiviral vector for stable and sustained expression of Tgif2 in liver cells. The inventors expressed Tgif2 in primary mouse hepatocytes that were freshly isolated from adult livers and cultured in standard hepatocyte culture medium (FIG. 2a). At one week after transduction with LV-TGIF2, the inventors measured robust ectopic Tgif2 expression and concomitant repression of liver-specific genes, including Albumin and Transthyretin (Ttr) and the transcription factors Hex, Hnf4a and Hnf4a1 liver-specific isoform (FIG. 2b). Two weeks post-transduction, the depletion of hepatic transcripts was maintained (FIG. 2b) and accompanied by induction of the pancreatic transcription factor, Pdx1 (FIG. 2b). Prolonged analysis of the LV-TGIF2-transduced cells beyond 2 weeks was not possible due to the short-term viability of primary hepatocyte culture in vitro (reference 40). Thus, to overcome this limitation, the inventors next used the well-characterized non-transformed BAML hepatic cell line (reference 41), as ex-vivo model system.

The BAML is a cell line established from adult mouse liver that was previously shown to retain hepatic differentiation hallmarks and repopulate the liver in vivo (reference 4) (FIG. 6). The inventors cultured the hepatic cells (hereafter referred to as HEP) in standard hepatocyte culture medium and characterized them after transduction with either LV-TGIF2 or LV-GFP, as control, at multiple time points ex vivo as well as in vivo (FIG. 2a). At early time points (1 and 2 weeks), ectopic Tgif2 expression in HEP cells elicited effects similar to those observed in primary hepatocytes, including strong reduction of hepatic gene expression program and induction of a set of pancreatic genes (FIG. 2c). Specifically, the inventors observed induction of the transcription factors Sox9 and Insm1 in Tgif2-expressing HEP already 1 week post-transduction, the earliest time-point studied, which was followed by induction of Pdx1 and Pax6 expression (FIG. 2c). Importantly, the levels of pancreatic transcripts either remained stably induced or increased (e.g. Pdx1, and MafA) over time [day (d) 30 and d50 time points after Tgif2 expression; FIG. 2c].

Repression of the hepatic gene expression program was also maintained in long-term cultures of LV-TGIF2-tranduced HEP cells, even though it became less prominent with time, suggesting possible occurrence of culture heterogeneity (FIG. 2c). Transcription factors in common between the two fates, such as Prox1 and Foxa2, were expressed at similar levels in both control and Tgif2-expressing HEP cells (FIG. 2c). Moreover, induction of Cdx2 expression was not detected in Tgif2-expressing HEP cells, ruling out the acquisition of duodenal or intestinal fates (FIG. 2c). Immunofluorescence analysis corroborated these findings, showing LV-TGIF2-tranduced HEP cells positive for GFP that were also positive for SOX9 and/or PDX1 but displayed reduction or loss of hepatic differentiation markers (Albumin and HNF4a; FIG. 2d).

Three weeks after transduction, a typical culture was composed of 50±4% SOX9-positive cells and 8.75±1.23% PDX1-positive cells, with an important fraction of the PDX1-positive cells (48.10±3.84%) co-expressing SOX9 (FIG. 2d). As expected, control hepatic cultures displayed nuclear HNF4a staining and typical abundant cytoplasmic albumin in the absence of pancreatic markers (FIG. 2d). Upon removal of dexamethasone from the culture, which is typically used to sustain hepatic phenotype and survival, the inventors observed a further increase of the expression levels of pancreatic progenitor transcription factors, but no acquisition of pancreatic functional differentiation (FIG. 6). Nevertheless, Tgif2-expressing HEP cells in modified medium occasionally displayed cytoplasmic granules, whose ultrastructure pattern resembled to that of immature pancreatic beta-cells (references 17, 22) (FIG. 1e).

Together, these results indicate that TGIF2 is sufficient to activate a typical pancreatic progenitor gene-expression signature in mature hepatocytes and efficiently silence molecular features characteristic of the starting cell population. Thus, TGIF2 dual activity enables to overcome a hybrid phenotype, inducing a stepwise cell identity switch. The reprogrammed HEP cells are hereafter referred to as TGIF2-induced Pancreatic Progenitor (TiPP) cells.

The inventors observed that Tgif2-expressing cells proliferated at a lower rate than controls during the first week after transduction and reacquired the normal proliferative activity after ten days. Consistently, at day 4 post-transduction the cells exhibited a lowered fraction of G1 cells and an increased percentage of cells in S-phase (FIG. 2e). These results suggest that the decreased proliferation rate observed in cells within the first week of reprogramming might be due to a partial arrest or delay of the S/G2 phase of the cell cycle. This is consistent with the fact that cell division is not required in many examples of somatic lineage reprogramming (references 4, 8).

Fate Conversion Recapitulates Early Stages of Pancreas Development

Next, to start elucidating the mechanisms underlying TGIF2-induced liver-to-pancreas conversion, the inventors analysed the changes in global gene expression in reprogrammed TiPP cells. The inventors compared the gene expression profiles of FACS-purified TiPP cells at two time points [14 d and 30 d post-transduction], control HEP cells, mouse embryonic pancreas (E14.5) and adult pancreas and liver tissues. Unsupervised hierarchical clustering of gene expression data showed a clear relationship between reprogrammed TiPP cells and E14.5 mouse pancreas (FIG. 3a). As expected, the control HEP population clustered together with adult liver (FIG. 3a). Notably, many representative genes of the pancreatic progenitor program, including Sox9, Pdx1, Ptf1a, Pax6, Insm1, Onecut1, Nr5a2, RbpJ, Tle2, Tle3, were upregulated in TiPP cells, whereas all well-known genes involved in hepatic functions, such as cytochrome enzymes, apolipoproteins and detoxification enzymes, were down-regulated (FIG. 7). Next, the inventors examined changes in gene expression associated with the initial events of reprogramming by focusing on analysis of the d14 time point. The inventors studied the overlap between the set of genes dysregulated in TiPP d14 cells during reprogramming and a set of 296 genes constituting an expression-signature of mouse E10.5 pancreatic progenitors (reference 24) (FIG. 3b). Importantly, the inventors found that more than 20% of the pancreas progenitor genes were upregulated in TiPP d14 cells, indicating a significant overlap (p-value<0.05) despite the methodological and temporal differences. Thus, the reprogramming event was broadly reflected in global gene expression changes, suggesting that TiPP cells are similar to mouse pancreatic progenitors.

Analysis of Gene Ontology (GO) terms enrichment of differentially regulated TiPP genes revealed enrichment for genes involved in metabolism, developmental processes, cell adhesion, transcription and signal transduction (FIG. 3c). Interestingly, the analysis of enrichment of Panther pathway annotations pointed to genes involved in the Wnt signaling pathway (23 genes; p-value, 0.00043) (FIG. 3d). In particular, the inventors found that many Wnt/Planar cell polarity (PCP) core genes, such as Stbm/Vangl, Fmi/Celsr, Prickle1 and Scrib, as well as downstream Wnt transducers, such as Tcf7, Nfatc2, Camk2b and Tle3, were upregulated in reprogrammed cells (FIG. 3e, f). These findings are consistent with the previously recognized role for non-canonical Wnt in pancreas and liver cell lineage divergence and imply concurrent changes in epithelial cell polarity during liver-to-pancreas fate conversion, as seen during pancreas progenitor development (references 24). In addition to Wnt modulation, the inventors found robust and stable upregulation of Fgfr1 and some of its well-known downstream signal transducers, including Akt3, Plcg2, Mapk12, Rasal1, in the reprogrammed TiPP cells when compared to control hepatocytes (FIG. 3b, f). Recent observations identified a regulatory loop between SOX9 and FGF signaling in the early pancreatic niche that is required to repress liver-specific gene expression program and ensure pancreatic fate identity at early time point (reference 42).

The findings described herein suggest that TGIF2 installs a similar circuit between SOX9 and FGFR1 in hepatocytes that undergo reprogramming, recapitulating the same mechanisms required to lock cell fate in pancreas progenitors in vivo (reference 42).

Induced Pancreatic Progenitors Differentiate In Vivo

A stringent test routinely used for pancreatic progenitor cells obtained in vitro is whether they 'mature' to functional cells when implanted in vivo (references 38, 39). Thus, to assess the in vivo differentiation potential of the reprogrammed-derived pancreatic progenitors, the inventors engrafted the TiPP cells under the kidney capsule of hyperglycemic Akita mice. Islets from Akita heterozygous mice are depleted of beta-cells, and the remaining beta-cells release very little mature insulin, representing an excellent mouse model of diabetes (references 43). The inventors found that blood glucose levels improved soon after transplantation of TiPP cells and remained stable over the eight weeks duration of the experiment (FIG. 4a).

Immunohistochemical analysis revealed that TiPP cells implanted under the kidney capsule organized themselves into epithelial structures, which were positive for SOX9, E-cadherin and insulin (FIG. 4b, FIG. 8a). By contrast, Akita mice transplanted with HEP cells transduced with control LV-GFP displayed higher levels of glycemia throughout the assay and did not acquire pancreatic differentiation features in the kidney mesenchyme (FIG. 4b). No tumors were observed after eight weeks posttransplantion. These results indicate that pancreatic progenitors derived from reprogrammed HEP cells are 'poised' for further differentiation along the endocrine beta-cell lineage when exposed to the appropriate environment. This is in line with the presence of cytoplasmic endocrine granules in TiPP cells, as detected by TEM (FIG. 2).

In Vivo Induction of Pancreas Progenitors

Next, the inventors asked the question whether TGIF2 might change cell fate identity and promote the pancreatic program in differentiated hepatic cells in vivo in the native liver environment. To this aim, the inventors ectopically expressed Tgif2 in adult hepatocytes using recombinant adeno-associated virus (AAV) vector (FIG. 4c). To exclusively target hepatocytes, the inventors chose the AAV serotype 8 (AAV2/8), which exhibits hepatocyte-specific tropism and rapid clearance, and combined it with the hepatocyte-specific thyroid-binding globulin (TBG) promoter (reference 44).

Livers from adult animals administered with AAV8.TBG-Tgif2 were collected at different time points after delivery and examined for cellular identity by immunofluorescence (FIG. 4c). As expected, intravenous administration of AAV8.TBG-Tgif2 vector resulted in robust ectopic expression of Tgif2 in the liver parenchyma (FIG. 8b). Normal tissue-architecture was preserved in AAV-injected livers, as judged by their lobular organization along the porto-central axis and distinct periportal and perivenous gene expression patterns (FIG. 4d). Notably, within 1 week of AAV8.TBG-Tgif2 injection, the inventors detected ectopic SOX9-positive cells throughout the liver parenchyma (FIG. 4d), whereas in adult livers under normal conditions SOX9 marks only biliary epithelial cells (BEC) (references 45, 46, 47) (FIG. 4d). This discrete ectopic SOX9 activation was found in AAV8.TBG-Tgif2-injected livers at all examined time points and various locations, including in the perivenous "zone 3" liver that is close to the central vein and, normally, positive for glutamine synthetase (GS) but negative for BEC markers (references 40, 44, 45) (FIG. 4d). Moreover, the inventors found activation of PDX1 expression in a small subset of SOX9-positive cells that were often, but not exclusively, located in the periportal region of the livers of AAV8.TBG-Tgif2-injected animals (FIG. 4d).

In summary, the results provided herein indicate that ectopically expressed TGIF2 exerts the same activity in vivo, being sufficient to induce the expression of Sox9 and Pdx1, during normal adult liver homeostasis. Given the fact that adult hepatocytes are differentiated and arrested in quiescence (G0 phase), the change in cell identity triggered by Tgif2 ectopic expression occurs in the absence of cell division, implying direct fate conversion of hepatocytes to a pancreatic progenitor state.

Production of Human TGIF2-Induced Pancreatic Progenitor Cells:

Cells obtained from a percutaneous liver biopsy from a human subject may be treated according to standard protocols and prepared for in vitro culture. The isolated cells are subsequently cultured under standard conditions for hepatic cells on collagen I-coated plates in William's E medium (SIGMA) supplemented with 2 mM Glutamax, 10% FBS (PAN Biotech™), 30 ng/mL IGF II (PeproTech™), 50 ng/mL EGF (PeproTech™), 10 μg/mL Insulin (ROCHE), 0.1 μm dexamethasone (SIGMA) and 10 μm nicotinamide (SIGMA).

The pPGK-TGIF2-2A-EGFP lentiviral expression vector (LV-TGIF2) was generated by cloning the cDNAs of human Tgif2, linked by the T2A self-cleaving sequence, into the pRRL.SIN.cPPT.PGK-GFP.WPRE lentiviral plasmid vector (ADDGENE plasmid 12252). Lentiviral particles were produced as previously described (reference 50).

Cells are subsequently transduced with LV at a MOI of 40. After transduction, TGIF2-mediated reprogramming is allowed to occur during culture in medium depleted of insulin, IGF II and dexamethasone (modified medium). Cells are subsequently assayed for expression of Albumin, Transthyretin (Ttr) and/or Serpina 1, and Pdx1, Sox9, Pax6 and/or Ptf1a. Upon detection of the desired expression characteristics re-programmed cells are harvested, washed and prepared in a suitable aqueous formulation for administration.

Production of Human TGIF2-Encoding Adeno-Associated Virus Vectors:

The adeno-associated viral construct AAV8.TBG.TGIF2 was generated by cloning human Tgif2cDNA into the pEN-N.AAV2/8.TBG.PI.RBG plasmid vector (PennVector p1015). Viral particles were produced as described herein and particles of adeno-associated virus diluted in sterile PBS for administration.

Experiments in Mouse Diabetic Models:

Akita mice are a recently described mouse mutant model of type I diabetes mellitus, whereby the disease arises as a result of selective pancreatic B-cell toxicity and depletion resulting from misfolding of insulin. The advantages of this model of type I diabetes are the early onset, progressive functional and structural glomerular injury and spontaneous diabetes development. This mouse model represents a valuable model for assessing potential human treatments.

AAV.TGIF2 vectors as described above are injected into Akita diabetic mouse models. The Blood Glucose (BG) levels of the injected animals are monitored over two months. After observation of amelioration of BG levels after 2 months, glucose tolerance tests and measurements of insulin levels in plasma of the injected animals are performed. The livers of injected animals are analyzed by histological analysis and immunofluorescence staining with antibodies against typical pancreatic and beta-cell markers.

As a control experiment, an AAV.GFP vector is injected into Akita diabetic mouse models and the same experiments are performed as above.

Amelioration of BG levels can be observed in treated subjects compared to controls. Glucose tolerance tests, insulin measurements and histological analysis of livers can indicate a therapeutic effect of the administered vector.

Experiments in Akita mouse models are being carried out using cellular therapy via administration of induced pancreatic progenitors into subjects via intravenous injection or injection into the liver of mouse subjects. The production of such cells is carried out as described herein. Therapeutic effects of the cellular therapy may be identified using the measurement of BG levels, glucose tolerance tests, insulin measurements and histological analysis of livers, as described above.

Reprogramming Experiments in Human Hepatocyte Models:

Human TGIF2-coding sequences (ORF) are cloned into the same AAV vector described in the above examples and as applied in mouse models. Human primary hepatocytes are exposed to the AAV.hTGIF2 vector in vitro and the phenotype of the cells is assessed using RT-qPCR, microarray and immunofluorescence staining for hepatic and pancreatic markers. Marker analysis indicates that re-programming of human cells occurs via repression of liver-specific markers and activation of pancreatic specific markers.

Experiments are performed in commercially available human primary hepatocytes (Invitrogen). Upon observation of similar fate conversion effects in the human cells as described herein for mouse cells, the same experiments using hepatocytes differentiated from iPS cells and from human liver biopsies are carried out. Human hepatocytes obtained from various sources are capable of undergoing the desired re-programming upon treatment with vectors encoding human TGIF2.

Experiments are also conducted using a lentiviral vector expressing the hTgif2 (LV-hTgif2) gene in frame with the GFP (Green Fluorescent Protein) reporter gene in commercially available primary human hepatocytes. Additional ex vivo human hepatocyte models will be established for studying fate conversion, including human hepatocytes derived from commercial iPS cells (ATCC). Human iPS cells are differentiated into hepatocytes according to published protocols, subsequently transduced with LV-hTgif2 and characterized for changes in cellular identity at different time points after transduction. Potential repression of hepatic gene expression program and induction of pancreatic gene expression program in the different LV-hTgif2-transduced human liver cells is analyzed by both RT-qPCR and immunofluorescence assays. Dose-response experiments using different LV titers at multiple time points (e.g. 1, 2, 4 and 6 weeks) enable determination of the ideal conditions for the hTgif2 reprogramming activity.

Discussion of the Experimental Examples

Evidence is presented herein that TGIF2 is a novel regulator of pancreas versus liver lineage fate decision in mammalian foregut progenitors and exerts a twofold reprogramming activity: i. it unlocks hepatic cell identity and promotes erasure of hepatic initial identity, and ii. it establishes pancreas cell identity. The hepatic cells undergoing fate switching pass through an intermediate state that lacks characteristics of both the initial and the final cellular identities, a so-called dedifferentiation step. Importantly, the inventors found that this intermediate state is not widely plastic and Tgif2-expressing cells are instead "lineage-restricted" toward the pancreatic progenitor fate, without reverting to pluripotency or switching to other closely related lineages. This reported stepwise fate conversion affords a unique opportunity to decipher genetic and epigenetic changes during the intermediate states of liver-to-pancreas reprogramming. This might also shed light on more fundamental reprogramming mechanisms. Indeed, fate conversion via successive steps, with a "tissue-restricted" dedifferentiation step preceding re-differentiation into the new cell type, has been reported in natural transdifferentiation events in worms (reference 48) as well as during limb regeneration in the axolotl (reference 49), suggesting possible common themes in reprogramming and regeneration across phyla.

The knowledge gained from these experimental manipulations has significant implications for clinical application. The stepwise TGIF2-dependent fate conversion represents a novel strategy for controlled generation of pancreatic progenitors from liver and an effective starting point for the production of pancreatic beta-cells suitable for therapeutic use in diabetic patients.

The success of this strategy in human cells offers the possibility of a renewable source of pancreatic cells, representing a significant advancement towards the development of an autologous cell therapy (donor and recipient are the same) to cure diabetes. The strategy described herein presents distinctive advantages over other potential cell-based therapeutic approaches for diabetes. Firstly, one key advantage is the use of liver cells as cellular source for the reprogramming. This approach would allow the diabetic patient to be the donor of his own therapeutic tissue. Liver biopsy is indeed well established in clinical practice, holding the potential for autologous cell therapy and eliminating the risk of graft-versus-host disease.

Secondly, lineage reprogramming of differentiated cells is more efficient than programming cell fate via the use of human embryonic stem (ES) or induced pluripotent stem (iPS) cells and lacks the risk of tumor formation, which remains an important concern for both ES and iPS cells. Thirdly, the strategy and reprogramming factor identified by the inventors presents important advantages over previous reprogramming approaches devised in either pancreas or liver cells. For instance, Tgif2 is a single factor with a dual activity, being able to erase hepatic features and promote pancreatic identity, and therefore reduces the risk due to incomplete reprogramming and hybrid cellular states.

Methods

Cell Culture and Viral Infection

R1 mESC line were cultured and differentiated as previously reported (reference 24). Mouse CD-1 primary hepatocytes and BAML cells were cultured on Collagen I-coated plates in hepatocyte medium (reference 41). Cells were infected with pPGK-TGIF2-2A-EGFP lentiviral expression vector (LV-TGIF2) at MOI of 40.

AAV Injection

Replication-incompetent AAV8.TBG.TGIF2 particles were produced at the Penn Vector Core facility. $2\text{-}4 \times 10^{11}$ particles of adeno-associated virus diluted in sterile PBS were administered per adult mouse (C57BL/6 strain) by tail vein injection.

Mouse Strains

C57BL/6-Ins2$^{Akita/}$J (reference 43), TGIF1$^{tm1aPah}$ (reference 33), Tg(Sox2-cre)$^{1Amc/J}$ and Flp-deleter (JAX laboratories) mouse strains were previously described. The mouse TGIF2$^{tm1a(EUCOMM)Wtsi}$ strain was generated at the ICS using the EUCOMM embryonic stem (ES) cell collection (reference 32). TGIF2$^{tm1a(EUCOMM)\ Wtsi}$ mice were first bred to Flp-deleter mice (reference 24) to generate a floxed allele and the subsequent breeding to a strain expressing Cre recombinase resulted in the knockout mouse. As Akita mice the insulin 2 Akita (Ins2Akita) model may be used. All animal experimentation was carried out in accordance to the local ethics committee for animal care.

Cell Culture and FACS Experiments mESCs (R1 mESC line) were maintained on gelatin-coated plates with mouse embryonic fibroblasts (MEFs) in standard mESC medium: DMEM (Invitrogen), 2 mM glutamax (Invitrogen), 1 mM sodium pyruvate (Invitrogen), 0.1 mM nonessential amino acids (Invitrogen), 15% fetal bovine serum (FBS) (PAN Biotech), 0.1 mM b-mercaptoethanol (Sigma), and 1000 U/mL leukemia inhibitory factor (ES- GRO). For differentiation, cultures were MEF-depleted and seeded in mESC medium at high confluency on gelatin-coated dishes. Monolayer differentiation was carried out as described previously (references 38, 39). Briefly, definitive endoderm (DE) medium to day 2 consisted of RPMI medium (Invitrogen) and 0.2% FBS supplemented with 50 ng/mL Activin A and 25 ng/mL Wnt3a at day 1 and Activin A only at day 2. Pancreatic endoderm (PE) medium to day 8 consisted of RPMI medium and 2% FBS supplemented with 3 ng/mL Wnt3a and 50 ng/mL FGF10. All recombinant proteins were purchased from R&D System unless otherwise stated. Plateable male mouse CD-1 cryopreserved primary hepatocytes were purchased (LIFE TECHNOLOGIES) and cultured on Collagen I-coated plates in William's E medium (Sigma) supplemented with 2 mM Glutamax, 10% FBS (PAN Biotech), 30 ng/mL IGF II (PeproTech™), 50 ng/mL EGF (PeproTech™), 10 µg/mL Insulin (ROCHE), 0.1 µm dexamethasone (SIGMA) and 10 µm nicotinamide (Sigma). The BAML cells were cultured in the same conditions as primary hepatocytes reference 41) (referred to as "HEP conditions"). When indicated, HEP cells were cultured in the absence of insulin, dexamethasone and IGF II (referred to as "modified medium"). For FACS isolation, hepatic cell suspensions were first filtered through a BD Falcon tube with cell strainer cap (BD 352235). Before sorting, propidium iodide (PI) was added to exclusively select live cells. After dead cell exclusion (SSC-A/PI-A), GFP-expressing cells were sorted using a FACS Aria I flow cytometer (BD Biosciences™) using a GFP filter and setting the gate on the GFP fluorescence intensity. Conditions of sorting were as follows: 70-mm nozzle and sheath pressure of 70 psi. For cell cycle analysis, cells were fixed in 70% ethanol overnight and incubated with 100 µg/mL RNase A and 40 µg/mL PI for 30 minutes at 37° C. The cell cycle profile was analyzed using the BD LSRFortessa cell analyzer.

Lentivirus Production

The pPGK-TGIF2-2A-EGFP lentiviral expression vector (LV-TGIF2) was generated by cloning the cDNAs of mouse Tgif2 and EGFP, linked by the T2A self-cleaving sequence, into the pRRL.SIN.cPPT.PGK-GFP.WPRE lentiviral plasmid vector (Addgene plasmid 12252). Lentiviral particles were produced as previously described (reference 50). Titration was performed in HEK 293 cells; cells were transduced with LV at a MOI of 40.

Reverse Transcription and Quantitative PCR

For RNA isolation, adult and embryonic tissues were dissected and snap-frozen on dry ice and RNA was extracted with RNAzol (BIOZOL) according to manufacturer's instructions. The High Pure RNA Isolation Kit (Roche) was used for RNA extraction from cultured cells. Total RNA was processed for reverse transcription (RT) using Transcriptor First Strand cDNA Synthesis Kit (ROCHE). A mix of anchored-Oligo(dT)18 and random hexamer primers was used to generate the cDNA. Real-time PCR reactions were carried out using the SYBR Green Master Mix (ROCHE) on ABI StepOne Plus™ system. Succinate dehydrogenase (SDHA) was used as reference gene. Primer sequences are provided Table 1. All the values were normalised to the reference genes and calculated using the software REST (reference 51). Data were determined in triplicates.

TABLE 1

| GENE SYMBO | FORWARD PRIMER | REVERSE PRIMER |
| --- | --- | --- |
| Alb | TGCTGCTGATTTTGTTGAGG (SEQ NO 5) | GCAGCACTTTTCCAGAGTGG (SEQ NO 6) |
| Cdx2 | AAACCTGTGCGAGTGGATG (SEQ NO 7) | CTGCGGTTCTGAAACCAAA (SEQ NO 8) |
| Celsr 1 | TGGTACCAGGGCAGGCTGTGCTTC (SEQ NO 9) | CCAGTGAAGCGCTGAGGGTGTG (SEQ NO 10) |
| Celsr3 | CCAGGCCAAGTCACACTTTTG (SEQ NO 11) | TAGGGATGGGCCATTGTGAGT (SEQ NO 12) |
| Cldn3 | CGTCAGTTTTCGAAGGGCAG (SEQ NO 13) | ATGGCTGCTGGACTTGAACC (SEQ NO 14) |
| Fgfr 1 | TGCCTGAACAAGATGCACTCCCA (SEQ NO 15) | TCTGGGGATGTCCAGTAGGGAGC (SEQ NO 16) |
| Foxa2 | CATCCGACTGGAGCAGCTA (SEQ NO 17) | GCGCCCACATAGGATGAC (SEQ NO 18) |
| Hex | GAGGTTCTCCAACGACCAGA (SEQ NO 19) | GTCCAACGCATCCTTTTTGT (SEQ NO 20) |
| Hnf4a | AACCACGCTACTTGCCTTTGCT (SEQ NO 21) | TCTGATGGGACACAGCCTACTTCT (SEQ NO 22) |
| Hnf4a 1 | GAAAATGTGCAGGTGTTGACCA (SEQ NO 23) | AGCTCGAGGCTCCGTAGTGTTT (SEQ NO 24) |
| Insraft 1 | GCCCAGGTGTTCCCCTGCAA (SEQ NO 25) | AGGCCCGGGGAGCTGTAGAA (SEQ NO 26) |
| Isl 1 | GCGGCCTCTGCAAATGGCAG (SEQ NO 27) | CTCCGGCTGCTTGTGGACGT (SEQ NO 28) |
| Mafa | GAGGTGAAGAAGGAGCCGCCC (SEQ NO 29) | CTGAGGGGCGTCGAGGACAG (SEQ NO 30) |
| Nexn | AGGAGGCGAGAAGGCACATGGTAA (SEQ NO 31) | CTGAGTTTGAGTTTTCCTGGGCGGT (SEQ NO 32) |
| Pax6 | CAACCTGCCTATGCAACCCCCA (SEQ NO 33) | GGGCAGCATGCACGAGTACGA (SEQ NO 34) |
| Pdx 1 | CCACCAAAGCTCACGCGTGGA (SEQ NO 35) | GGCGGGGCCGGGAGATGTATT (SEQ NO 36) |
| Prox 1 | CCGACATCTCACCTTATTGAG (SEQ NO 37) | TGCGAGGTAATGCATCTGTTG (SEQ NO 38) |
| Ror2 | CTATATGTGCGGCTCGGTCC (SEQ NO 39) | AGGTGCCGATCATGGTGAAG (SEQ NO 40) |
| Scrib | AGTCTGCAGAGACCACGGGTCG (SEQ NO 41) | ATGGCTGGATCACCCCCGGTT (SEQ NO 42) |

TABLE 1-continued

| GENE SYMBO | FORWARD PRIMER | REVERSE PRIMER |
|---|---|---|
| SDHA | TGTTCAGTTCCACCCCACA (SEQ NO 43) | TCTCCACGACACCCTTCTGT (SEQ NO 44) |
| Sox1 7 | GGTCTGAAGTGCGGTTGG (SEQ NO 45) | TGTCTTCCCTGTCTTGGTTGA (SEQ NO 46) |
| Sox9 | AGACTCACATCTCTCCTAATGCT (SEQ NO 47) | ACGTCGGTTTTGGGAGTGG (SEQ NO 48) |
| Tead2 | CTGGACAGGTAGCGAGGAAG (SEQ NO 49) | GTTCCGGCCATACATCTTGC (SEQ NO 50) |
| Tgif2 | CTATCTGCACCGCTACAACG (SEQ NO 51) | GGGCATTGATGAACCAGTTAC (SEQ NO 52) |
| Ttr | CGTTCCATGAATTCGCGGATGTGGT (SEQ NO 53) | GCAGGGCTGCGATGGTGTAGT (SEQ NO 54) |
| Vangl2 | CAGCTCCCGGAAGCACAGGGAC (SEQ NO 55) | GTGCCCGTGACCACCGTTGT (SEQ NO 56) |

Transmission Electron Microscopy

Cells were fixed in phosphate-buffered 2.5% glutaraldehyde for 4 hours at 4° C. and postfixed in 1% OsO4. Samples were dehydrated and embedded in epoxy resin. Thin sections were counterstained with uranil acetate and lead citrate and examined with a HITACHI H-7100FA microscope.

Immunohistochemistry and In Situ Hybridization

Mouse embryos and tissues were fixed in 4% paraformaldehyde at 4° C. from 2 hours to overnight. Whole-mount immunostainings on embryos were performed as previously described (references 24, 26). Whole mouse embryos from E 9.5 onward were cleared in methyl salicylate for confocal microscope imaging. Whole-mount in situ hybridization was performed as described (reference 26). For cryosectioning, samples were equilibrated in 20% sucrose solution and embedded in OCT compound (SAKURA). In situ hybridization on cryostat sections (10 µm) was carried out as previously described (reference 26). For immunostaining, cryosections were incubated with TSA (PERKIN ELMER) blocking buffer for 1 hour at room temperature (RT) and afterwards with primary antibodies at the appropriate dilution. If necessary, antigen retrieval was performed by boiling the slides for 20 minutes in citrate buffer (DAKO). For immunofluorescence on cultured cells, cells were grown on coverslips, fixed in 4% paraformaldehyde for 20 minutes at RT and permeabilized in 0.2% Triton X-100 in PBS. Unspecific binding was blocked using 3% donkey serum and 0.1% Triton X-100 in PBS for 30 minutes at RT and incubation with antibodies was performed in blocking solution (Table 2). Hoechst 33342 counterstaining was used at a concentration of 20 µg/mL. Images were acquired on ZEISS AxioObserver™ and ZEISS LSM 700 laser scanning microscope. Huygens software (SVI) was used for 3D volume measurement analysis of confocal z-stacks.

TABLE 2

| Antibody | Catalog number | Host Species | Dilution |
|---|---|---|---|
| anti-ALBUMIN | DAKOCYTOMATION, A0001 | Rabbit | 1:100 |
| anti-E CADHERIN | INVITROGEN, 13-1900 | Rat | 1:1000 |
| anti-FOXA2 | ABCAM, AB408749 | rabbit | 1:200 |
| anti-GFP | AVES, GFP-1020 | chicken | 1:500 |
| anti-GFP | ABCAM, AB290 | rabbit | 1:500 |
| anti-HNF4a | Santa Cruz, sc-6556 | goat | 1:100 |
| anti-INSULIN | INVITROGEN, 18-0067 | guinea pig | 1:250 |
| anti-PDX1 | ABCAM, ab 408749 | rabbit | 1:200 |
| anti-PDX1 | ABCAM, ab 47308 | guinea pig | 1:500 |
| anti-PROX1 | CHEMICON, AB5475 | rabbit | 1:500 |
| anti-PROX1 | RELIATech GmbH, 102PA32S | rabbit | 1:200 |

TABLE 2-continued

| Antibody | Catalog number | Host Species | Dilution |
|---|---|---|---|
| anti-SOX17 | R&D Systems | goat | 1:100 |
| anti-SOX9 | Uni Nurnberg, Uni 09-1 | rabbit | 1:500 |
| anti-SOX9 | MILLIPORE, AB5535 | rabbit | 1:500 |
| anti-TGIF2 | ABNOVA, H00060436-A01 | mouse | 1:200 |
| anti-TGIF2 | ABNOVA, H00060436-M01 | mouse | 1:200 |

Microarray and Bioinformatic Methods

Whole transcriptome analysis was performed on AGILENT SurePrint G3 Mouse GE 8x60K Microarray Kits™ at the MPI Array Facility, Dresden. The single color signals were read using Agilent Feature Extraction Software. All bioinformatic analyses were performed using R (http://www.r-project.org). Differential gene expression was determined using the R statistical package limma (reference 52). Adjusted p-values were corrected for multiple testing using the Benjamini-Hochberg method. Gene Ontology analysis was performed using the Genecodis application (reference 53).

Transplantation Underneath the Kidney Capsule

Spontaneously diabetic 8-9 weeks old C57BL/6-Ins2$^{Akita}$/J female mice were used as recipients. FACS-sorted cells were collected and transplanted under the kidney capsule, according to previously reported procedures (reference 54). Blood glucose was measured at 12 h intervals over the first two days post-transplantation and biweekly thereafter. After 8 weeks, the graft-bearing kidneys were removed and fixed overnight in 4% formalin at RT. Samples were embedded in paraffin for histological analysis.

AAV Experiments

The adeno-associated viral construct AAV8.TBG.TGIF2 was generated by cloning mouse Tgif2 cDNA into the pENN.AAV2/8.TBG.PI.RBG plasmid vector (PennVector p1015). Replication-incompetent AAVs were produced at the Penn Vector Core facility. 2-4×10$^{11}$ particles of adeno-associated virus diluted in sterile P BS were administered per adult mouse (C57BL/6 strain) by tail vein injection.

Statistical Tests

All results are expressed as mean±standard errors (SEM). The significance of differences between groups was evaluated with Student's t-test or ANOVA test. $P<0.05$ was considered statistically significant. Statistictical tests relevant to the microarray analysis are described in the Bioinformatic Analysis section.

REFERENCES

1 Gurdon, J. From nuclear transfer to nuclear reprogramming: the reversal of cell differentiation. *Annu Rev Cell Dev Biol.* 22, 1-22 (2006).

2 Slack, J. M. Metaplasia and transdifferentiation: from pure biology to the clinic. *Nat. Rev. Mol. Cell Biol.* 8, 369-378 (2007).

3 Takahashi, K. & Yamanaka, S. Induction of pluripotent stem cells from mouse embryonic and adult fibroblast cultures by defined factors. *Cell* 126, 663-676 (2006).

4 Graf, T. & Enver, T. Forcing cells to change lineages. *Nature* 3, 587-594 (2009).

5 Jopling, C., Boue, S. & Izpisua Belmonte, J. Dedifferentiation, transdifferentiation and reprogramming: three routes to regeneration. *Nat Rev Mol Cell Biol.* 12, 79-89 (2011).

6 Vierbuchen, T. & Wernig, M. Direct lineage conversions: unnatural but useful? *Nat. Biotechnol.* 29, 892-907 (2011).

7 Thorel, F. et al. Conversion of adult pancreatic alpha-cells to beta-cells after extreme beta-cell loss. *Nature* 464, 1149-1154 (2010).

8 Zhou, Q., Brown, J., Kanarek, A., Rajagopal, J. & Melton, D. A. In vivo reprogramming of adult pancreatic exocrine cells to beta-cells. *Nature* 455, 627-632 (2008).

9 Al-Hasani, K. et al. Adult duct-lining cells can reprogram into beta-like cells able to counter repeated cycles of toxin-induced diabetes. *Dev Cell* 26, 86-100 (2013).

10 Bonner-Weir, S. et al. In vitro cultivation of human islets from expanded ductal tissue. *Proc Natl Acad Sci USA.* 97, 7999-8004 (2000).

11 Baeyens, L. et al. Transient cytokine treatment induces acinar cell reprogramming and regenerates functional beta cell mass in diabetic mice. *Nat Biotechnol.* 32, 76-83 (2014).

12 Bramswig, N. C. et al. Epigenomic plasticity enables human pancreatic alpha to beta cell reprogramming. *J Clin Invest* 123, 1275-1284 (2013).

13 Hesselson, D., Anderson, R. M. & Stainier, D. Y. Suppression of Ptf1a activity induces acinar-to-endocrine conversion. *Curr Biol* 21, 712-717 (2011).

14 Lee, J. et al. Expansion and conversion of human pancreatic ductal cells into insulin-secreting endocrine cells. *Elife* 2, e00940 (2013).

15 Yang, Y. P., Thorel, F., Boyer, D. F., Herrera, P. L. & Wright, C. V. Context-specific alpha-to-beta-cell reprogramming by forced Pdx1 expression. *Genes Dev* 25, 1680-1685 (2011).

16 Horb, M. E., Shen, C. N., Tosh, D. & Slack, J. M. Experimental conversion of liver to pancreas. *Curr Biol* 13, 105-115, doi:S0960982202014343 [pii](2003).

17 Banga, A., Akinci, E., Greder, L. V., Dutton, J. R. & Slack, J. M. In vivo reprogramming of Sox9+ cells in the liver to insulin-secreting ducts. *Proc Natl Acad Sci USA* 109, 15336-15341 (2012).

18 Ferber, S. et al. Pancreatic and duodenal homeobox gene 1 induces expression of insulin genes in liver and ameliorates streptozotocin-induced hyperglycemia. *Nat Med* 6, 568-572 (2000).

19 Nagaya, M., Katsuta, H., Kaneto, H., S, B.-W. & Weir, G. Adult mouse intrahepatic biliary epithelial cells induced in vitro to become insulin-producing cells. *J Endocrinol.* 201, 37-47 (2009).

20 Wang, A. Y., Ehrhardt, A., Xu, H. & Kay, M. A. Adenovirus transduction is required for the correction of diabetes using Pdx-1 or Neurogenin-3 in the liver. *Mol Ther* 15, 255-263 (2007).

21 Yechoor, V. et al. Neurogenin 3 is sufficient for transdetermination of hepatic progenitor cells into neo-islets in vivo but not transdifferentiation of hepatocytes. *Dev Cell* 16, 358-373 (2009).

22 Puri, S. & Hebrok, M. Cellular Plasticity within the Pancreas-Lessons Learned from Development. *Developmental Cell* 18, 342-356 (2010).

23 Zaret, K. & Grompe, M. Generation and regeneration of cells of the liver and pancreas. *Science* 322, 1490-1494 (2008).

24 Rodriguez-Seguel, E. et al. Mutually exclusive signaling signatures define the hepatic and pancreatic progenitor cell lineages divergence. *Genes Dev.* 27, 1932-1946 (2013).

25 Xu, C. R. et al. Chromatin "prepattern" and histone modifiers in a fate choice for liver and pancreas. *Science* 332, 963-966 (2011).

26 Spagnoli, F. M. & Brivanlou, A. H. The Gata5 target, TGIF2, defines the pancreatic region by modulating BMP signals within the endoderm. *Development* 135, 451-461 (2008).

27 Cerda-Esteban, N. & Spagnoli, F. M. A Glimpse Into Hox and Tale Regulation of Cell Differentiation and Reprogramming. *Dev Dynamics* 243, 76-87 (2014).

28 Kim, S. et al. Pbx1 inactivation disrupts pancreas development and in Ipf1-deficient mice promotes diabetes mellitus. *Nat. Genetics* 30, 430-435 (2002).

29 Moens, C. B. & Selleri, L. Hox cofactors in vertebrate development. *Dev Biol.* 291, 193-206 (2006).

30 Tremblay, K. D. & Zaret, K. S. Distinct populations of endoderm cells converge to generate the embryonic liver bud and ventral foregut tissues. *Dev. Biol.* 280, 87-99 (2005).

31 Powers, S. et al. Tgif1 and Tgif2 regulate Nodal signaling and are required for gastrulation. *Development* 137, 249-259 (2010).

32 Ryder, E. et al. Molecular Characterization of Mutant Mouse Strains Generated from the EUCOMM/KOMP-CSD ES Cell Resource. *Mamm Genome* 24, 286-294 (2013).

33 Mar, L. & Hoodless, P. A. Embryonic Fibroblasts from Mice Lacking Tgif Were Defective in Cell Cycling. *Mol Cell Biol* 26, 4302-4310 (2006).

34 Choi, E. et al. Dual lineage-specific expression of Sox17 during mouse embryogenesis. *Stem Cells* 30, 2297-2308 (2012).

35 Engert, S., Burtscher, I., Kalali, B., Gerhard, M. & Lickert, H. The Sox17CreERT2 knock-in mouse line displays spatiotemporal activation of Cre recombinase in distinct Sox17 lineage progenitors. *Genesis* 51, 793-802 (2013).

36 Kanai-Azuma, M. et al. Depletion of definitive gut endoderm in Sox17-null mutant mice. *Development* 129, 2367-2379 (2002).

37 Spence, J. R. et al. *Sox17* regulates organ lineage segregation of ventral foregut progenitor cells. *Dev Cell* 17, 62-74 (2009).

38 D'Amour, K. et al. Production of pancreatic hormone-expressing endocrine cells from human embryonic stem cells. *Nat. Biotechnol.* 24, 1392-1401 (2006).

39 Nostro, M. et al. Stage-specific signaling through TGF-beta family members and WNT regulates patterning and pancreatic specification of human pluripotent stem cells. *Development* 138, 861-871 (2011).

Michalopoulos, G. K. Liver regeneration. *J Cell Physiol* 213, 286-300 (2007).

41 Fougere-Deschatrette, C. et al. Plasticity of hepatic cell differentiation: bipotential adult mouse liver clonal cell lines competent to differentiate in vitro and in vivo. *Stem Cells* 24, 2098-2109 (2006).

42 Seymour, P. A. et al. A Sox9/Fgf feed-forward loop maintains pancreatic organ identity. *Development* 139, 3363-3372 (2012).
43 Yoshioka, M., Kayo, T., Ikeda, T. & Koizumi, A. A novel locus, Mody4, distal to D7Mit189 on chromosome 7 determines early-onset NIDDM in nonobese C57BL/6 (Akita) mutant mice. *Diabetes* 46, 887-894 (1997).
44 Yanger, K. et al. Robust cellular reprogramming occurs spontaneously during liver regeneration. *Genes Dev* 27, 719-724 (2013).
Carpentier, R. et al. Embryonic ductal plate cells give rise to cholangiocytes, periportal hepatocytes, and adult liver progenitor cells. *Gastroenterology* 141, 1432-1438 (2011).
46 Dorrell, C. et al. Prospective isolation of a bipotential clonogenic liver progenitor cell in adult mice. *Genes Dev* 25, 1193-1203 (2011).
47 Kopp, J. L. et al. Sox9+ ductal cells are multipotent progenitors throughout development but do not produce new endocrine cells in the normal or injured adult pancreas. *Development* 138, 653-665, (2011).
48 Richard, J. P. et al. Direct in vivo cellular reprogramming involves transition through discrete, non-pluripotent steps. *Development* 138, 1483-1492 (2011).
49 Kragl, M. et al. Cells keep a memory of their tissue origin during axolotl limb regeneration. *Nature* 460, 60-65 (2009).
50 Tiscornia, G., Singer, O. & Verma, I. Production and purification of lentiviral vectors. *Nat Protocoll,* 241-245 (2006).
51 Pfaffl, M. W., Horgan, G. W. & Dempfle, L. Relative expression software tool (REST©) for group-wise comparison and statistical analysis of relative expression results in real-time PCR. *Nucleic Acids Research* 30, e36 (2002).
52 Smyth, G. K. *Limma: Linear Models for microarray data. In: Bioinformatics and Computational Biology Solutions using R and Bioconductor.* 397-420 (Springer, New York, 2005).
53 Nogales-Cadenas, R. et al. GeneCodis: interpreting gene lists through enrichment analysis and integration of diverse biological information. *Nucleic Acids Res.* 37, W137-122 (2009).
54 Borg, D. et al. Mesenchymal stromal cells improve transplanted islet survival and islet function in a syngeneic mouse model. *Diabetologia* Epub November 20 (2013).

What we claim is:

1. A method for treatment of a human subject with diabetes or a pre-diabetic human subject, comprising: administering to the subject with diabetes or the pre-diabetic subject genetically modified human pancreatic progenitor cells in an amount effective to treat the subject with diabetes or the pre-diabetic subject, wherein said human pancreatic progenitor cells modified by an exogenous nucleic acid molecule encoding a single transcription factor, wherein the transcription factor is TGFB-induced factor homeobox 2 (TGIF2), and wherein said cells differentiate in vivo into cells of the endocrine beta-cell lineage, and wherein the genetically modified human pancreatic progenitor cells are obtained from human adult hepatocytes via TGIF2-induced re-programming.

2. The method of claim 1, wherein the genetically modified human pancreatic progenitor cells are autologous to the subject with diabetes or the pre-diabetic subject.

3. The method of claim 1, wherein the exogenous nucleic acid further comprises a phosphoglycerate kinase-1 (PGK) promoter operably linked to a nucleic acid sequence encoding the TGIF2.

4. The method of claim 1, wherein said treatment comprises cellular therapy comprising intravenous administration of the genetically modified human pancreatic progenitor cells.

5. The method of claim 1, wherein the genetically modified human pancreatic progenitor cells exhibit repression of liver-specific gene expression and activation of pancreas-specific gene expression.

6. The method of claim 5, wherein the repression of liver-specific gene expression comprises repression of one or more genes selected from the group consisting of Albumin, Transthyretin (Ttr), Serpina 1, Hex, Hnf4 (Hepatocyte nuclear factor 4)-alpha and Hnf4-alpha1 liver-specific isoform.

7. The method of claim 6, wherein the repression of liver-specific gene expression comprises repression of Albumin, Transthyretin (Ttr) and Serpina 1.

8. The method of claim 5, wherein the activation of pancreas-specific gene expression comprises activation of one or more genes selected from the group consisting of Pdx1 (pancreatic and duodenal homeobox 1), Sox9 (SRY (sex determining region Y)-box 9), Insm1 (insulinoma-associated 1), Pax6 (Paired box protein 6), Ptf1 a (pancreas specific transcription factor 1 a), Onecut1 (one cut homeobox 1), Nr5a2 (Nuclear Receptor Subfamily 5, Group A, Member 2), RbpJ (Recombination Signal Binding Protein For Immunoglobulin Kappa J Region), Tle2 (Transducin-Like Enhancer Of Split 2), Tle3 (Transducin-Like Enhancer Of Split 3) and MafA (v-maf musculoaponeurotic fibrosarcoma oncogene family, protein A).

9. The method of claim 8, wherein the activation of pancreas-specific gene expression comprises activation of Pdx1, Sox9 and Ptf1a.

10. The method of claim 1, wherein the exogenous nucleic acid comprises an adeno-associated viral vector (AAV).

11. The method of claim 10, wherein the adeno-associated viral vector (AAV) is AAV2/8.

* * * * *

SEQUENCE LISTING

```
<160> NUMBER OF SEQ ID NOS: 56

<210> SEQ ID NO 1
<211> LENGTH: 237
<212> TYPE: PRT
<213> ORGANISM: Homo sapiens

<400> SEQUENCE: 1

Met Ser Asp Ser Asp Leu Gly Glu Asp Gly Leu Leu Ser Leu Ala
1               5                   10                  15

Gly Lys Arg Lys Arg Gly Asn Leu Pro Lys Glu Ser Val Lys Ile
            20                  25                  30

Leu Arg Asp Trp Leu Tyr Leu His Arg Tyr Asn Ala Tyr Pro Ser Glu
            35                  40                  45

Gln Glu Lys Leu Ser Leu Ser Gly Gln Thr Asn Leu Ser Val Leu Gln
        50                  55                  60

Ile Cys Asn Trp Phe Ile Asn Ala Arg Arg Arg Leu Leu Pro Asp Met
65                  70                  75                  80

Leu Arg Lys Asp Gly Lys Asp Pro Asn Gln Phe Thr Ile Ser Arg Arg
                85                  90                  95

Gly Gly Lys Ala Ser Asp Val Ala Leu Pro Arg Gly Ser Ser Pro Ser
            100                 105                 110

Val Leu Ala Val Ser Val Pro Ala Pro Thr Asn Val Leu Ser Leu Ser
        115                 120                 125

Val Cys Ser Met Pro Leu His Ser Gly Gln Gly Glu Lys Pro Ala Ala
    130                 135                 140

Pro Phe Pro Arg Gly Glu Leu Glu Ser Pro Lys Pro Leu Val Thr Pro
145                 150                 155                 160

Gly Ser Thr Leu Thr Leu Leu Thr Arg Ala Glu Ala Gly Ser Pro Thr
                165                 170                 175

Gly Gly Leu Phe Asn Thr Pro Pro Thr Pro Pro Glu Gln Asp Lys
            180                 185                 190

Glu Asp Phe Ser Ser Phe Gln Leu Leu Val Glu Val Ala Leu Gln Arg
        195                 200                 205
```

Ala Ala Glu Met Glu Leu Gln Lys Gln Gln Asp Pro Ser Leu Pro Leu
210 215 220

Leu His Thr Pro Ile Pro Leu Val Ser Glu Asn Pro Gln
225 230 235

<210> SEQ ID NO 2
<211> LENGTH: 3456
<212> TYPE: DNA
<213> ORGANISM: Homo sapiens

<400> SEQUENCE: 2

| | | | | | |
|---|---|---|---|---|---|
| ccgacggccc | gccccgcggg | gggtgggcgc | agctcgtcgc | gctccgcaca | aagtttgttt | 60 |
| tctccctccg | ggcgggtggg | ggagggcgca | gagggcgcgg | ggggaggaga | ggggatctga | 120 |
| cgtcaggccg | cgaggtgctt | tccagccgcg | agctgtcagg | ccgagtgtca | ggccgggcag | 180 |
| gtttacccaa | ggtccagcct | agcccctagg | caccatgtcg | acagtgatc | taggtgagga | 240 |
| cgaaggcctc | ctctccctgg | cgggcaaaag | gaagcgcagg | gggaacctgc | ccaaggagtc | 300 |
| ggtgaagatc | ctccgggact | ggctgtactt | gcaccgctac | aacgcctacc | cctcagagca | 360 |
| ggagaagctg | agccttttctg | gacagaccaa | cctgtcagtg | ctgcaaatat | gtaactggtt | 420 |
| catcaatgcc | cggcggcggc | ttctcccaga | catgcttcgg | aaggatggca | agaccctaa | 480 |
| tcagtttacc | atttcccgcc | gcggggggtaa | ggcctcagat | gtggccctcc | ccgtggcag | 540 |
| cagcccctca | gtgctggctg | tgtctgtccc | agcccccacc | aatgtgctct | ccctgtctgt | 600 |
| gtgctccatg | ccgcttcact | caggccaggg | ggaaaagcca | gcagcccctt | tcccacgtgg | 660 |
| ggagctggag | tctcccaagc | ccctggtgac | ccctggtagc | acacttactc | tgctgaccag | 720 |
| ggctgaggct | ggaagcccca | caggtggact | cttcaacacg | ccaccaccca | caccccccaga | 780 |
| gcaggacaaa | gaggacttca | gcagcttcca | gctgctggtg | gaggtggcgc | tacagagggc | 840 |
| tgctgagatg | gagcttcaga | agcagcagga | cccatcactc | ccattactgc | acactcccat | 900 |
| cccctttagtc | tctgaaaatc | cccagtaggc | atctgccaag | aagggtgctg | aaggctccag | 960 |
| ccagctgtcc | tgggtttccg | ttttggttcc | ctttcataca | gagggttttc | tatggatcac | 1020 |
| tgccaaacat | tgggatcatc | tcctctgtcc | agaggtcttc | aacaggaaga | tgccagctgg | 1080 |
| caccactgca | ctgtgatggg | ggccctctcc | tctgctgact | ctgccgtttc | tccaggcctc | 1140 |
| cgctcagtga | tgagaccaag | agatcggaga | caagcatggt | gctgctgctt | ctgctgcttc | 1200 |
| tccagaaaat | ccctgggaca | cctttgttcc | agcctggttt | cctgggctgg | gctcaggaaa | 1260 |
| gctgccaaat | tcagtcctat | gttgggtcca | agctgcccct | gtgctgtttc | tgtcaagcca | 1320 |
| ggtgtggaca | ttccaagttc | atatgcgtga | acaaagaaa | agaggaaccc | agtggatgta | 1380 |
| acagaaccga | ctccagttga | atgtttagat | ttttgctaaa | ctgttttctt | tttcccttt | 1440 |
| ttgctgtggt | ttgcattcac | ggcagtagtt | agcccaggtg | tggggaacga | gagtgcactg | 1500 |
| catgatagcg | ttctggtgag | ctgggaagga | cccaccactg | ccactgagga | ttgttttgga | 1560 |
| agaaaggaat | atttttatct | tggggaccag | ctaagtctct | gcagtagtgt | gaaattccaa | 1620 |
| atggttgttt | tatcattggt | ttggtttacc | aaaaaaaagg | cagggaaaaa | aaaaaaaaac | 1680 |
| aaccgtatga | gcgcattggc | ttgtctgccg | caggcacaga | agggtagaaa | gccacagcag | 1740 |
| ggggcagtcc | agcagactct | gactcaactt | tctaggcacc | tagcagagaa | agataagatc | 1800 |
| aaaaggtgtt | tggttttttct | tttaatttt | attgtagtt | ttttgggtgg | gtggggaag | 1860 |
| taaactagac | tgaagcgatg | gatttttttt | ttcttttttt | tctttagtgt | ttttcccttt | 1920 |

```
gttcttgaac acttttgccc tgcagcctca gttttgaatt cttttagcaa cttggattag    1980
aggggcccat atgtcagaag ctcccagcac ctcctacttg ggagaaaagt gagccatctg    2040
ctggtcagga agtcctccag agaggcagct tttcccacaa tggtggcagg aaactttggg    2100
gaaagcagga atggtgtcca ctgctgcgga ggaactgcct tcagagaagg tggggctgga    2160
aaagggttag aagcctccta gctgggattg tctttgtttc acctttcttt aaattagaat    2220
tacagaagcc cctgcccagt gaacagataa cgattggtct tatgctcctc cctttccccc    2280
atttttcctt ttgctgtttt gttttttgtt ttttgtttgt ttgtttgttt ttttgagaca    2340
gagtcatgct ctgtcacccg ggctggagtg cagtggtgcg atctcagctc actgtaacct    2400
ccgcctcccg ggttcaagca attatttgcc tcagcctccc gagtagctgg gattataggc    2460
acccgccacc atgtctggct tttagtagag acggggtttc accatcttgg ccaggctggt    2520
cttgaactc ctgacctcgt gagccaccac gcccagcctc ttttgctgtt tcattgctga     2580
cagtgttcaa caatatgccc catctttata tatcctaaga aacactaatc ctaggttatt    2640
gctagccaaa atatttttgt cctgagtagt gtcactgggc aaaagatag atcaggacga     2700
cagcctttag ttttcctgaa atcaccaggt caggcacaag gagaaaaggt tcctggatac    2760
tgactaactt gggtgggtct agccaggaga agacagtaa catgtgttct gtactttctg     2820
ggaagatccc tgaagccatc acagaggctc cccaacttct gagtcgccca tctgttgctg    2880
tgggagtgtg aacggatcgc tgaaggagag ggagctttgc tctctctagg tgggcaagtt    2940
tcctgggctc tctgtgttgc ctccctctgg cttcttcctc ccgtgccctc tccccgtgtg    3000
ccccaggggg atcagggatc ctcacccctcc tgaggcccag tggggaagaa tgaacatggc    3060
ttcatccagg ttaactgatg ctgccatttg cccagcctct tccatcccag ccctgtcagt    3120
gagcccaggt ctggtgcaac tgctgcagga tgcctgtagt agggaactct ggaagtgtat    3180
tgggctgagg tgggattttc cctccccaca gtgcactgag caatggaggg tggtgaggga    3240
gccatgctgc tgaattctgg ttggcatttc cccattatgt aaaatggggt gttgggtagg    3300
gcagactctg cttgggtttg gttgtaagat aaacctggag gagaagcaca gttgtcccat    3360
tgaattattt gagcaaaaac tactgtaaat aacttttttg tcttttgtca aataaaattt    3420
ttttttgttt ttttaagcag aaacaaaaaa aaaaaa                              3456
```

<210> SEQ ID NO 3
<211> LENGTH: 237
<212> TYPE: PRT
<213> ORGANISM: Mus musculus

<400> SEQUENCE: 3

```
Met Ser Asp Ser Asp Leu Gly Glu Asp Glu Gly Leu Leu Ser Leu Thr
1               5                   10                  15

Gly Lys Arg Lys Arg Gly Asn Leu Pro Lys Glu Ser Val Lys Ile
            20                  25                  30

Leu Arg Asp Trp Leu Tyr Leu His Arg Tyr Asn Ala Tyr Pro Ser Glu
        35                  40                  45

Gln Glu Lys Leu Ser Leu Ser Gly Gln Thr Asn Leu Ser Val Leu Gln
    50                  55                  60

Ile Cys Asn Trp Phe Ile Asn Ala Arg Arg Arg Leu Leu Pro Asp Met
65                  70                  75                  80

Leu Arg Lys Asp Gly Lys Asp Pro Asn Gln Phe Thr Ile Ser Arg Arg
                85                  90                  95

Gly Gly Lys Ala Ser Asp Val Ala Leu Pro Arg Gly Ser Ser Pro Ser
```

-continued

```
                     100                 105                 110
Leu Leu Ala Val Ser Val Pro Ala Pro Thr Asn Met Leu Ser Leu Ser
            115                 120                 125

Val Cys Ser Met Pro Leu His Ser Gly Gln Gly Glu Lys Pro Ala Ala
130                 135                 140

Pro Phe Pro Gln Val Glu Leu Glu Ser Pro Lys Ala Leu Val Thr Pro
145                 150                 155                 160

Ala Ser Thr Leu Thr Leu Leu Thr Arg Ala Glu Ala Gly Ser Pro Thr
                165                 170                 175

Gly Gly Leu Phe Asn Thr Pro Pro Thr Pro Pro Glu Gln Asp Lys
            180                 185                 190

Asp Asp Phe Ser Ser Phe Gln Leu Leu Val Glu Val Ala Leu Gln Arg
            195                 200                 205

Ala Ala Glu Met Glu Leu Gln Lys Gln Gln Glu Pro Ala Pro Pro Leu
        210                 215                 220

Leu His Thr Pro Leu Pro Phe Val Ser Glu Asn Ala Lys
225                 230                 235

<210> SEQ ID NO 4
<211> LENGTH: 2900
<212> TYPE: DNA
<213> ORGANISM: Mus musculus

<400> SEQUENCE: 4
ccacgctctg cacaaagttt gtttctgcct cggggcggtg ggggagggtg cggcaggcgg      60
gatgggagga gaggggatct gacgtcaggt cgcgaggtgc tttccagccg cgagctgtca     120
ggcgggtgtc agacccggca ggtacgcggc gcgttccccc ggtgccccc gccccggccg     180 ggtggtccca caccccaccg aggccgcgtg gccggaaag ccgccaggga aggctcccca     240
gaggtccagc ttagccccta agcatcatgt cggacagcga tctaggcgag gatgaggggc     300
tcctgtcact gaccggcaag aggaagcgca gaggaaccct gcccaaggag tcagtaaaga     360
tcctccggga ctggctctat ctgcaccgct acaacgccta cccctcagag caggagaagc     420
taagtctctc tggacagacc aacctctcgg tgctgcagat atgtaactgg ttcatcaatg     480
cccgtcgtcg ccttctccct gacatgcttc ggaaggatgg caaagaccct aatcagttca     540
ccatctcccg tcgtgggggt aaggcctctg atgtggctct ccccagggc agcagccccct     600 ctctgctggc tgtgtctgtt ccagccccca ctaacatgct ctccttgtct gtgtgctcca     660
tgccactcca ctcaggccaa ggtgaaaagc cagcagcacc cttccacaa gtggagctgg     720 aatccccccaa ggccctggtg acccctgcta gcacactcac cctgctgact agggcagagg     780
ctggaagccc cacgggtgga ctcttcaata cgccaccacc cacacccca gagcaggaca     840 aggatgactt cagcagcttc cagttgctgg tggaggtggc gctgcagagg gctgccgaga     900
tggagcttca gaagcagcaa gagccagcgc accttttgct acacactccg ctgcctttcg     960
tctcagaaaa cgccaagtag gcacctgctc ccgggtggc tgaggttcct ggctcactgc    1020
cctttcatgc agagggttat ccaagtacgg atcactgcca agcatcagga ccattctgtc    1080
cagtcctcag cggatgtcgc tgcgctgcac tgttacgggg cctgtactct gctgagtgcc    1140
attccttcaa gcgtcctctc cgaggagacc aaggcaccag agccaggcat ggtgttgctg    1200
ctgctcctcc agagagccct gggacacctg cactccagcc tgctttccta ggcaggctca    1260
ggaaagctgc caagtccaga cttgagctgg gtccaagccg cccctaagct gtgcctcttt    1320
tggtcgagcc aggtgtgcac attccaacct attcaaagga caaggaaat gcccagcaga    1380
```

-continued

```
tgtcacagaa ccgactccag ttgaatgttt agattttttgc taaattgttt tattttcctt   1440
ttgctgtggt ttgtgttaat gcagtaggta gcccagaagc acaggtgtgg ggagagagca   1500
ccttacacgg tgggtggagc tcggtaagtg ggtaatctac ttcccacagg atggttgtat   1560
agggaccagc agattctctg cagtggtgct gagttcagac tagagtggtt gtttaattct   1620
tggtttggtc ttccctatta taaaagacag aaggaaaata tccacaggtg gtgggttatt   1680
tgcaccagac ggtcatttag acacagcaga gacagatgac aaaaccagag gcacacgtgt   1740
ttctattgtc gtggttaagc tagagtgaaa cagctctgtt tttctctctg ttctgagtaa   1800
ctcccctcac cccaccccag cgaccccccac cctgcaccac ctttgtagct tgtttcggat   1860
ttattctgga gcttggcaag aatgtcgtgt gccagcatct acttgggagg agtgagccat   1920
ctgctggtca ttaggcccctt cggaaagctg cttgttcaca gaggcagctg gaaccttcct   1980
ggaggagagg ctgctgaggc taccgactgg cccacctccc ttcagggtgg gattgcaagg   2040
gcctgcctaa atttcccggg gaaacagacc acacttggtc ttaatctctc ccctttttccc   2100 gtttactttg cttagttttc agcaacagta taccccatct ttatatccta agaaacacta   2160
atcctagatt tgtattaacc aaaatacttg tgttctgaat aaccagaaga tgtgaggagc   2220
cctgactgtg gtctgaggtt cacccgggtg tgagcacaga cggggctctt ggatgttgac   2280
tggcttggag tgcctgttcc gaggaaggca gagaccactc tggcctttcc agggagcccc   2340
tgaggcttag caggcttcca tacctctcct gagtgacttc acccatccct tgctgtgcaa   2400
gtgggcgcga gaatggctat ttgtaagggg ctgcttccct gggctctgcc tcatgcctcc   2460
ctctggcttc ctgtcctgta ggagacccag caggctcaac tctctgtcac cctgaggcac   2520
tgctgggaag ggaacatggc ttcattgact ttgtggtttg cccactgcta ccccaccctgt   2580 ctgtgagacc ccatgatggc tgtaggatgc taaggcgggg gtgatactag gatgagggat   2640
ttcttttccc cccacagtgc actgagcaag ggaggaggga gggagccatg ctgctgacat   2700
attctggcat tccccctcct gggataaaac agggcatcag aaaggtagag cggtctctgc   2760
ttaggttgcc tgtaagataa atgtggagaa gcacggttgt cccattgaac aatatttgag   2820
caaaaaacta ctgtaaataa ctggttttttg tcttttgtca aataaaattg ttttggtttt   2880
gtttatgttt taaagtcaaa                                               2900
```

<210> SEQ ID NO 5
<211> LENGTH: 20
<212> TYPE: DNA
<213> ORGANISM: Mus musculus

<400> SEQUENCE: 5

```
tgctgctgat tttgttgagg                                                 20
```

<210> SEQ ID NO 6
<211> LENGTH: 20
<212> TYPE: DNA
<213> ORGANISM: Mus musculus

<400> SEQUENCE: 6

```
gcagcacttt tccagagtgg                                                 20
```

<210> SEQ ID NO 7
<211> LENGTH: 19
<212> TYPE: DNA
<213> ORGANISM: Mus musculus

<400> SEQUENCE: 7
aaacctgtgc gagtggatg                                            19

<210> SEQ ID NO 8
<211> LENGTH: 19
<212> TYPE: DNA
<213> ORGANISM: Mus musculus

<400> SEQUENCE: 8
ctgcggttct gaaaccaaa                                            19

<210> SEQ ID NO 9
<211> LENGTH: 24
<212> TYPE: DNA
<213> ORGANISM: Mus musculus

<400> SEQUENCE: 9
tggtaccagg gcaggctgtg cttc                                      24

<210> SEQ ID NO 10
<211> LENGTH: 22
<212> TYPE: DNA
<213> ORGANISM: Mus musculus

<400> SEQUENCE: 10
ccagtgaagc gctgagggtg tg                                        22

<210> SEQ ID NO 11
<211> LENGTH: 21
<212> TYPE: DNA
<213> ORGANISM: Mus musculus

<400> SEQUENCE: 11
ccaggccaag tcacactttt g                                         21

<210> SEQ ID NO 12
<211> LENGTH: 21
<212> TYPE: DNA
<213> ORGANISM: Mus musculus

<400> SEQUENCE: 12
tagggatggg ccattgtgag t                                         21

<210> SEQ ID NO 13
<211> LENGTH: 20
<212> TYPE: DNA
<213> ORGANISM: Mus musculus

<400> SEQUENCE: 13
cgtcagtttt cgaagggcag                                           20

<210> SEQ ID NO 14
<211> LENGTH: 20
<212> TYPE: DNA
<213> ORGANISM: Mus musculus

<400> SEQUENCE: 14
atggctgctg gacttgaacc                                           20

<210> SEQ ID NO 15
<211> LENGTH: 23
<212> TYPE: DNA
<213> ORGANISM: Mus musculus

<400> SEQUENCE: 15
tgcctgaaca agatgcactc cca                                              23

<210> SEQ ID NO 16
<211> LENGTH: 23
<212> TYPE: DNA
<213> ORGANISM: Mus musculus

<400> SEQUENCE: 16
tctggggatg tccagtaggg agc                                              23

<210> SEQ ID NO 17
<211> LENGTH: 19
<212> TYPE: DNA
<213> ORGANISM: Mus musculus

<400> SEQUENCE: 17
catccgactg gagcagcta                                                   19

<210> SEQ ID NO 18
<211> LENGTH: 18
<212> TYPE: DNA
<213> ORGANISM: Mus musculus

<400> SEQUENCE: 18
gcgcccacat aggatgac                                                    18

<210> SEQ ID NO 19
<211> LENGTH: 20
<212> TYPE: DNA
<213> ORGANISM: Mus musculus

<400> SEQUENCE: 19
gaggttctcc aacgaccaga                                                  20

<210> SEQ ID NO 20
<211> LENGTH: 20
<212> TYPE: DNA
<213> ORGANISM: Mus musculus

<400> SEQUENCE: 20
gtccaacgca tcctttttgt                                                  20

<210> SEQ ID NO 21
<211> LENGTH: 22
<212> TYPE: DNA
<213> ORGANISM: Mus musculus

<400> SEQUENCE: 21
aaccacgcta cttgcctttg ct                                               22

<210> SEQ ID NO 22
<211> LENGTH: 24
<212> TYPE: DNA
<213> ORGANISM: Mus musculus

<400> SEQUENCE: 22
tctgatggga cacagcctac ttct                                             24

<210> SEQ ID NO 23
<211> LENGTH: 22
<212> TYPE: DNA

<213> ORGANISM: Mus musculus

<400> SEQUENCE: 23
gaaaatgtgc aggtgttgac ca                                    22

<210> SEQ ID NO 24
<211> LENGTH: 22
<212> TYPE: DNA
<213> ORGANISM: Mus musculus

<400> SEQUENCE: 24
agctcgaggc tccgtagtgt tt                                    22

<210> SEQ ID NO 25
<211> LENGTH: 20
<212> TYPE: DNA
<213> ORGANISM: Mus musculus

<400> SEQUENCE: 25
gcccaggtgt tccctgcaa                                        20

<210> SEQ ID NO 26
<211> LENGTH: 20
<212> TYPE: DNA
<213> ORGANISM: Mus musculus

<400> SEQUENCE: 26
aggcccgggg agctgtagaa                                       20

<210> SEQ ID NO 27
<211> LENGTH: 20
<212> TYPE: DNA
<213> ORGANISM: Mus musculus

<400> SEQUENCE: 27
gcggcctctg caaatggcag                                       20

<210> SEQ ID NO 28
<211> LENGTH: 20
<212> TYPE: DNA
<213> ORGANISM: Mus musculus

<400> SEQUENCE: 28
ctccggctgc ttgtggacgt                                       20

<210> SEQ ID NO 29
<211> LENGTH: 21
<212> TYPE: DNA
<213> ORGANISM: Mus musculus

<400> SEQUENCE: 29
gaggtgaaga aggagccgcc c                                     21

<210> SEQ ID NO 30
<211> LENGTH: 20
<212> TYPE: DNA
<213> ORGANISM: Mus musculus

<400> SEQUENCE: 30
ctgaggggcg tcgaggacag                                       20

<210> SEQ ID NO 31
<211> LENGTH: 24

<212> TYPE: DNA
<213> ORGANISM: Mus musculus

<400> SEQUENCE: 31
aggaggcgag aaggcacatg gtaa                                          24

<210> SEQ ID NO 32
<211> LENGTH: 25
<212> TYPE: DNA
<213> ORGANISM: Mus musculus

<400> SEQUENCE: 32
ctgagtttga gttttcctgg gcggt                                         25

<210> SEQ ID NO 33
<211> LENGTH: 22
<212> TYPE: DNA
<213> ORGANISM: Mus musculus

<400> SEQUENCE: 33
caacctgcct atgcaacccc ca                                            22

<210> SEQ ID NO 34
<211> LENGTH: 21
<212> TYPE: DNA
<213> ORGANISM: Mus musculus

<400> SEQUENCE: 34
gggcagcatg cacgagtacg a                                             21

<210> SEQ ID NO 35
<211> LENGTH: 21
<212> TYPE: DNA
<213> ORGANISM: Mus musculus

<400> SEQUENCE: 35
ccaccaaagc tcacgcgtgg a                                             21

<210> SEQ ID NO 36
<211> LENGTH: 21
<212> TYPE: DNA
<213> ORGANISM: Mus musculus

<400> SEQUENCE: 36
ggcggggccg ggagatgtat t                                             21

<210> SEQ ID NO 37
<211> LENGTH: 21
<212> TYPE: DNA
<213> ORGANISM: Mus musculus

<400> SEQUENCE: 37
ccgacatctc accttattga g                                             21

<210> SEQ ID NO 38
<211> LENGTH: 21
<212> TYPE: DNA
<213> ORGANISM: Mus musculus

<400> SEQUENCE: 38
tgcgaggtaa tgcatctgtt g                                             21

<210> SEQ ID NO 39

```
<210> SEQ ID NO 39
<211> LENGTH: 20
<212> TYPE: DNA
<213> ORGANISM: Mus musculus

<400> SEQUENCE: 39
ctatatgtgc ggctcggtcc                                           20

<210> SEQ ID NO 40
<211> LENGTH: 20
<212> TYPE: DNA
<213> ORGANISM: Mus musculus

<400> SEQUENCE: 40
aggtgccgat catggtgaag                                           20

<210> SEQ ID NO 41
<211> LENGTH: 22
<212> TYPE: DNA
<213> ORGANISM: Mus musculus

<400> SEQUENCE: 41
agtctgcaga gaccacgggt cg                                        22

<210> SEQ ID NO 42
<211> LENGTH: 21
<212> TYPE: DNA
<213> ORGANISM: Mus musculus

<400> SEQUENCE: 42
atggctggat caccccggt t                                          21

<210> SEQ ID NO 43
<211> LENGTH: 19
<212> TYPE: DNA
<213> ORGANISM: Mus musculus

<400> SEQUENCE: 43
tgttcagttc cacccaca                                             19

<210> SEQ ID NO 44
<211> LENGTH: 20
<212> TYPE: DNA
<213> ORGANISM: Mus musculus

<400> SEQUENCE: 44
tctccacgac accttctgt                                            20

<210> SEQ ID NO 45
<211> LENGTH: 18
<212> TYPE: DNA
<213> ORGANISM: Mus musculus

<400> SEQUENCE: 45
ggtctgaagt gcggttgg                                             18

<210> SEQ ID NO 46
<211> LENGTH: 21
<212> TYPE: DNA
<213> ORGANISM: Mus musculus

<400> SEQUENCE: 46
tgtcttccct gtcttggttg a                                         21
```

```
<210> SEQ ID NO 47
<211> LENGTH: 23
<212> TYPE: DNA
<213> ORGANISM: Mus musculus

<400> SEQUENCE: 47
agactcacat ctctcctaat gct                                               23

<210> SEQ ID NO 48
<211> LENGTH: 19
<212> TYPE: DNA
<213> ORGANISM: Mus musculus

<400> SEQUENCE: 48
acgtcggttt tgggagtgg                                                    19

<210> SEQ ID NO 49
<211> LENGTH: 20
<212> TYPE: DNA
<213> ORGANISM: Mus musculus

<400> SEQUENCE: 49
ctggacaggt agcgaggaag                                                   20

<210> SEQ ID NO 50
<211> LENGTH: 20
<212> TYPE: DNA
<213> ORGANISM: Mus musculus

<400> SEQUENCE: 50
gttccggcca tacatcttgc                                                   20

<210> SEQ ID NO 51
<211> LENGTH: 20
<212> TYPE: DNA
<213> ORGANISM: Mus musculus

<400> SEQUENCE: 51
ctatctgcac cgctacaacg                                                   20

<210> SEQ ID NO 52
<211> LENGTH: 21
<212> TYPE: DNA
<213> ORGANISM: Mus musculus

<400> SEQUENCE: 52
gggcattgat gaaccagtta c                                                 21

<210> SEQ ID NO 53
<211> LENGTH: 25
<212> TYPE: DNA
<213> ORGANISM: Mus musculus

<400> SEQUENCE: 53
cgttccatga attcgcggat gtggt                                             25

<210> SEQ ID NO 54
<211> LENGTH: 21
<212> TYPE: DNA
<213> ORGANISM: Mus musculus

<400> SEQUENCE: 54
gcagggctgc gatggtgtag t                                                 21
```

```
<210> SEQ ID NO 55
<211> LENGTH: 22
<212> TYPE: DNA
<213> ORGANISM: Mus musculus

<400> SEQUENCE: 55
cagctcccgg aagcacaggg ac                                              22

<210> SEQ ID NO 56
<211> LENGTH: 20
<212> TYPE: DNA
<213> ORGANISM: Mus musculus

<400> SEQUENCE: 56
gtgcccgtga ccaccgttgt                                                 20
```